(12) United States Patent
Erramilli et al.

(10) Patent No.: US 10,806,498 B2
(45) Date of Patent: Oct. 20, 2020

(54) INSTRUMENTS AND RELATED METHODS FOR BREAKING REDUCTION TABS

(71) Applicant: Medos International Sarl, Le Locle (CH)

(72) Inventors: Seetal Erramilli, Mulgrave (AU); Frank Spratt, Middleboro, MA (US); Grant Mellor, Eltham (AU); Chris Culhane, Chadstone (AU); Ben Stungo, Templestowe (AU); Joanna Talis, Lane Cove (AU)

(73) Assignee: Medos International Sarl, Le Locle (CH)

(*) Notice: Subject to any disclaimer, the term of this patent is extended or adjusted under 35 U.S.C. 154(b) by 72 days.

(21) Appl. No.: 15/458,194

(22) Filed: Mar. 14, 2017

(65) Prior Publication Data

US 2018/0263675 A1    Sep. 20, 2018

(51) Int. Cl.
*A61B 17/70* (2006.01)
*A61B 17/88* (2006.01)

(52) U.S. Cl.
CPC ...... *A61B 17/8863* (2013.01); *A61B 17/7074* (2013.01); *A61B 17/7079* (2013.01)

(58) Field of Classification Search
CPC .............. A61B 17/708; A61B 17/8863; A61B 17/7074; A61B 17/7082; A61B 17/7091
See application file for complete search history.

(56) References Cited

U.S. PATENT DOCUMENTS

| | | | |
|---|---|---|---|
| 6,736,820 B2 | 5/2004 | Biedermann et al. | |
| 6,974,460 B2 | 12/2005 | Carbone et al. | |
| 7,179,261 B2 | 2/2007 | Sicvol et al. | |
| 9,402,673 B2 | 8/2016 | Cormier et al. | |
| 9,743,958 B2 * | 8/2017 | Ishii | A61B 17/7032 |
| 9,968,394 B2 * | 5/2018 | Meyer | A61B 17/7074 |
| 2012/0031792 A1 * | 2/2012 | Petit | A61B 50/30 206/438 |
| 2014/0094862 A1 | 4/2014 | Cormier et al. | |
| 2016/0113685 A1 * | 4/2016 | Ishii | A61B 17/7037 606/266 |
| 2016/0296266 A1 | 10/2016 | Chandanson et al. | |
| 2016/0346017 A1 * | 12/2016 | Meyer | A61B 17/7074 |

OTHER PUBLICATIONS

[NoAuthorListed] Expedium Verse® Spinal System, System Guide, 2015, 52 pages.

* cited by examiner

*Primary Examiner* — Zade Coley

(74) *Attorney, Agent, or Firm* — Nutter McClennen & Fish LLP

(57) ABSTRACT

Instruments and related methods for breaking reduction tabs are disclosed herein, e.g., for breaking reduction tabs of a bone anchor or other implant. In some embodiments, the instrument can be configured to minimize the space needed to operate the instrument. For example, the instrument can be configured to receive a reduction tab that is to be broken while the instrument is coaxially positioned with respect to a bone anchor receiver to which the reduction tab is attached. As another example, the instrument can have a maximum outer transverse dimension that is less than, equal to, or only slightly greater than a corresponding dimension of a bone anchor from which a reduction tab is to be broken. Guide rods for positioning a tab breaker instrument over a reduction tab are also disclosed.

20 Claims, 20 Drawing Sheets

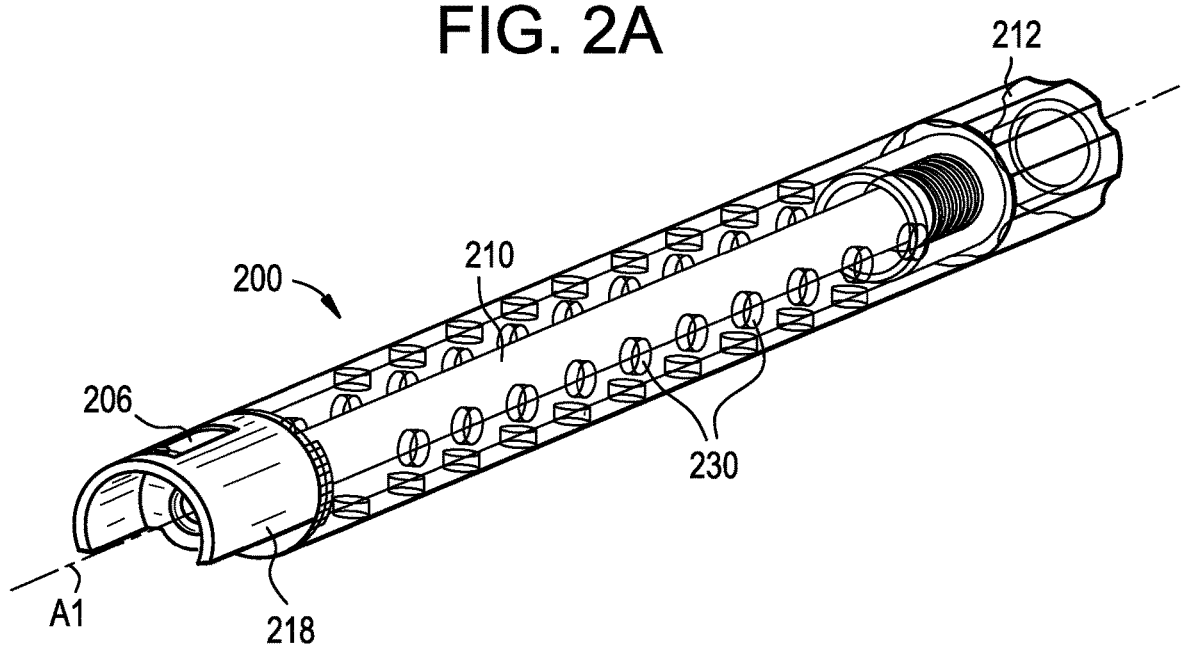
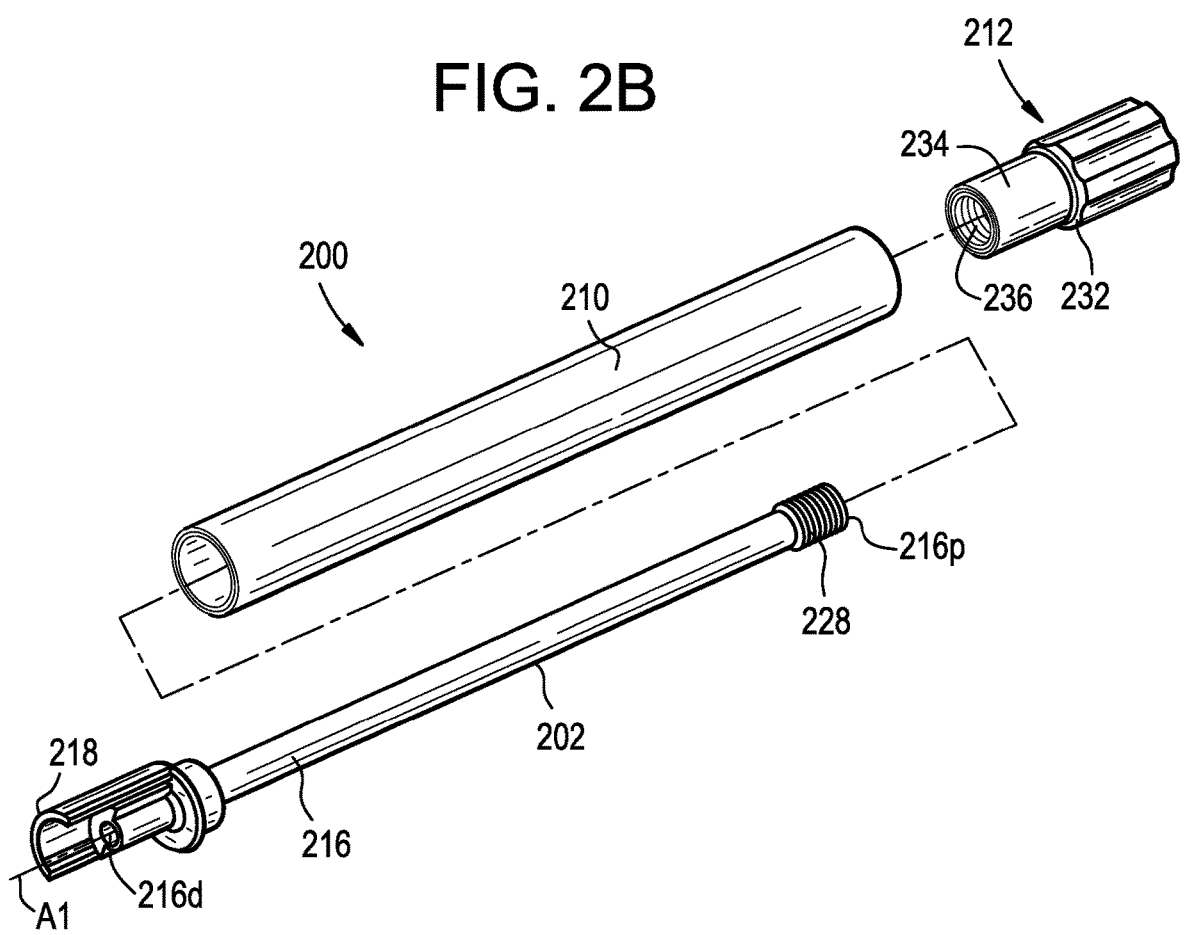

INSTRUMENTS AND RELATED METHODS FOR BREAKING REDUCTION TABS

FIELD

Instruments and related methods for breaking reduction tabs are disclosed herein, e.g., for breaking reduction tabs of a bone anchor or other implant.

BACKGROUND

Bone anchors can be used in orthopedic surgery and/or neurosurgery to fix bone during healing, fusion, or other processes. In spinal surgery, for example, bone anchors can be used to secure a rod or other spinal fixation element to one or more vertebrae to rigidly or dynamically stabilize the spine.

Some bone anchors have one or more reduction tabs (which may sometimes be referred to as extension tabs) extending proximally from the head of the bone anchor. For example, a conventional bone anchor configured to receive an elongate spinal rod can include first and second opposed reduction tabs on either side of the bone anchor's rod recess. The reduction tabs can be used to guide insertion of a rod into the rod recess, to provide a mechanical advantage when reducing a rod into the rod recess, to guide insertion of a set screw or other fastener component of the bone anchor, or for various other purposes. Reduction tabs are sometimes used, alone or in combination with other instrumentation, to provide a percutaneous or minimally-invasive working channel between an implanted bone anchor and a skin incision. Reduction tabs are usually designed to be broken off or otherwise separated from the bone anchor once they are no longer needed to complete the surgery. The broken reduction tabs are removed from the patient before closing the surgical wound and are then discarded.

Various instruments have been developed to assist a user in breaking off the reduction tabs. Such instruments can be bulky or can have a geometry that renders them poorly suited for certain use cases, such as in percutaneous or minimally-invasive procedures or in other situations where access or available space is limited. Such instruments can also be difficult to align with the reduction tab to be broken off, particularly when used with reduction tabs that are shorter than the depth of the incision in which they are placed.

SUMMARY

Instruments and related methods for breaking reduction tabs are disclosed herein, e.g., for breaking reduction tabs of a bone anchor or other implant. In some embodiments, the instrument can be configured to minimize the space needed to operate the instrument. For example, the instrument can be configured to receive a reduction tab that is to be broken while the instrument is coaxially positioned with respect to a bone anchor receiver to which the reduction tab is attached. As another example, the instrument can have a maximum outer transverse dimension that is less than, equal to, or only slightly greater than a corresponding dimension of a bone anchor from which a reduction tab is to be broken. Guide rods for positioning a tab breaker instrument over a reduction tab are also disclosed.

In some embodiments, an instrument for breaking reduction tabs can include a first shaft having a first opening configured to receive a reduction tab; a second shaft having a second opening configured to receive a reduction tab; and a cap that retains proximal ends of the shafts to one another. The cap can be removable to allow the first and second shafts to be independently spread apart from one other to break reduction tabs received within the openings of the first and second shafts.

The instrument can include a first retention element disposed in association with the first opening to retain a broken reduction tab within the first opening and a second retention element disposed in association with the second opening to retain a broken reduction tab within the second opening. The first and second shafts can together define an inner cannulation that is coaxial with a cannulation of the cap. The first and second openings can be formed as a negatives of respective sections of a tube. The first opening can be defined between an outer surface of a body portion of the first shaft and an inner surface of a first shroud extending distally from the body portion. The second opening can be defined between an outer surface of a body portion of the second shaft and an inner surface of a second shroud extending distally from the body portion. The first and second shrouds can be connected to their respective body portions by opposed struts. The first and second shrouds can define a complete tube. The instrument can include a first chamber in communication with the first opening and configured to store broken reduction tabs and a second chamber in communication with the second opening and configured to store broken reduction tabs. The first and second chambers can be defined between inner body portions of the first and second shafts and outer sleeve portions of the first and second shafts. The first shaft can include an inner abutment surface that contacts a counterpart inner abutment surface of the second shaft. The first and second shafts can include outer surfaces that collectively define a complete tube. The inner surfaces can be substantially planar. The inner surface of the first shaft can include a male mating feature received within a female mating feature of the inner surface of the second shaft. The cap can include first and second arms received within corresponding channels formed in proximal ends of the first and second shafts.

In some embodiments, a reduction tab breaking system can include a bone anchor having a receiver head with a central longitudinal axis and first and second reduction tabs extending proximally from the receiver head; and an instrument for breaking the reduction tabs off of the receiver head, the instrument comprising a shaft that defines an opening sized to receive one of the reduction tabs therein. A central longitudinal axis of the shaft can be collinear with the central longitudinal axis of the receiver head when one of the reduction tabs is received within the opening.

The instrument can have a maximum outer transverse dimension that is less than or equal to a maximum outer transverse dimension of the bone anchor. The system can include a guide rod having a distal portion configured to be secured to the bone anchor and a proximal guide shaft received within a central cannulation of the instrument to guide one of the reduction tabs of the bone anchor into the opening. The distal portion of the guide rod can include a plug with a distal projection sized to be received within a drive recess of a fastener of the bone anchor and one or more radial projections configured to engage threads of the bone anchor. The plug can be rotatable relative to the guide shaft about an axis perpendicular to a longitudinal axis of the guide shaft. The instrument can include a shroud that defines at least a portion of the opening, the shroud having an inside diameter that is substantially equal to an outside diameter of the first and second reduction tabs. The opening can have a cross-section in a plane transverse to a central longitudinal axis of the instrument that is substantially the same as a corresponding cross section of one of the first and second reduction tabs.

In some embodiments, a method of breaking a reduction tab can include advancing a tab breaker instrument over first and second reduction tabs extending proximally from a receiver of a bone anchor such that the first reduction tab is received within a first opening of a first shaft of the instrument, such that the second reduction tab is received within a second opening of a second shaft of the instrument, and such that a central longitudinal axis of the instrument is collinear with a central longitudinal axis of the receiver; and manipulating the first and second shafts to break the first and second reduction tabs off of the receiver.

Manipulating the shafts can include separating the shafts such that a central longitudinal axis of the first shaft is obliquely angled with respect to a central longitudinal axis of the second shaft and with respect to the central longitudinal axis of the receiver. Manipulating the shafts can include independently: (i) obliquely angling the first shaft relative to the receiver to break the first reduction tab; and (ii) obliquely angling the second shaft relative to the receiver to break the second reduction tab. Manipulating the shafts can include obliquely angling both shafts in the same direction relative to the receiver while sliding one shaft longitudinally along the other shaft. The method can include attaching a guide rod to the bone anchor and inserting the instrument over a guide shaft of the guide rod to guide the first and second reduction tabs into the first and second openings. The bone anchor can be implanted in a bone of a patient such that the reduction tabs do not protrude above a skin surface of the patient.

BRIEF DESCRIPTION OF THE DRAWINGS

FIG. 2A is a perspective view of an instrument that can be used to break reduction tabs;

FIG. 2B is an exploded perspective view of the instrument of FIG. 2A;

DETAILED DESCRIPTION

Instruments and related methods for breaking reduction tabs are disclosed herein, e.g., for breaking reduction tabs of a bone anchor or other implant. In some embodiments, the instrument can be configured to minimize the space needed to operate the instrument. For example, the instrument can be configured to receive a reduction tab that is to be broken while the instrument is coaxially positioned with respect to a bone anchor receiver to which the reduction tab is attached. As another example, the instrument can have a maximum outer transverse dimension that is less than, equal to, or only slightly greater than a corresponding dimension of a bone anchor from which a reduction tab is to be broken. Guide rods for positioning a tab breaker instrument over a reduction tab are also disclosed.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Prior Art Bone Anchor

Figure 1A:
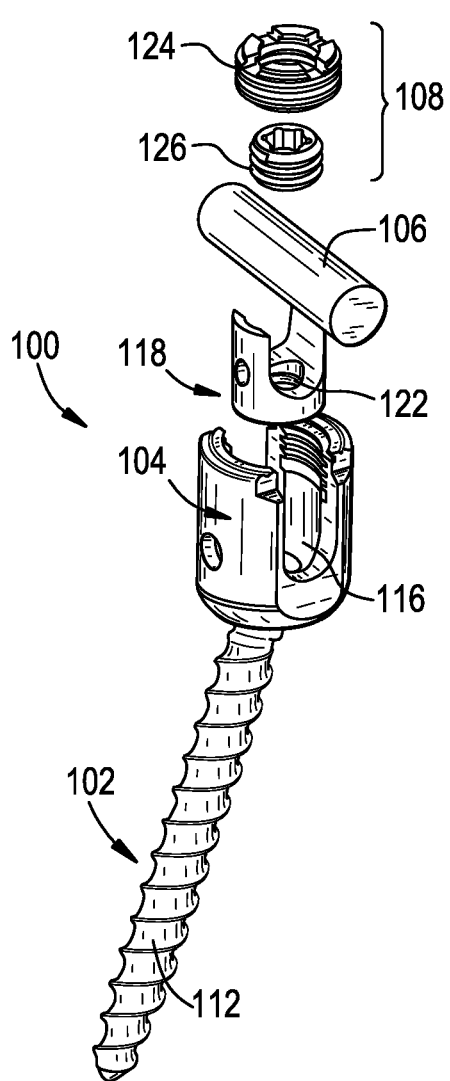
FIG. 1A is an exploded perspective view of a prior art bone anchor.
Figure 1B:
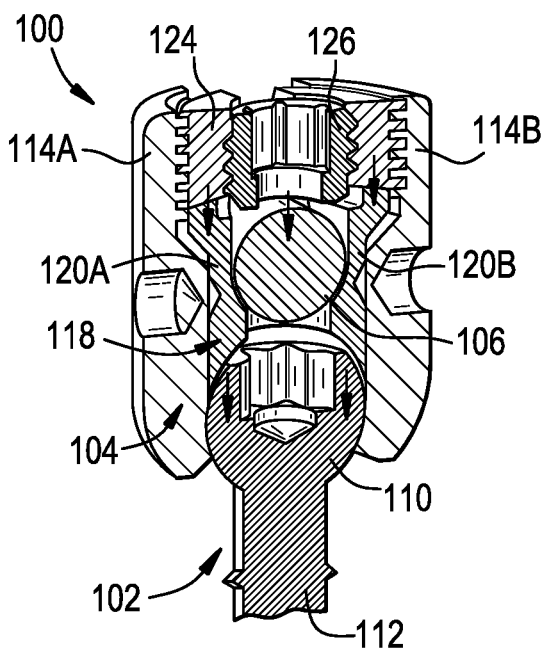
FIG. 1B is a sectional perspective view of the bone anchor of FIG. 1A.
Figure 1C:
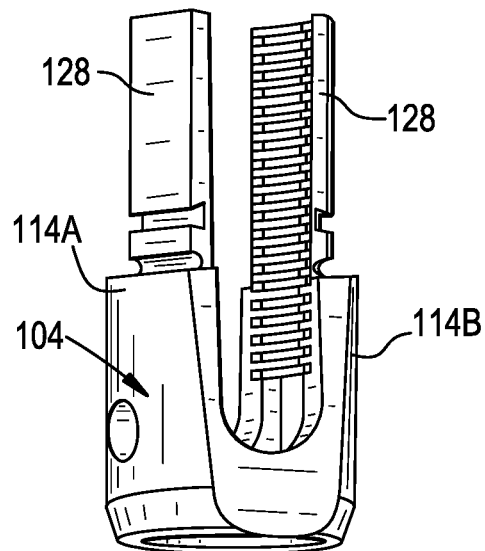
FIG. 1C is a perspective view of a receiver member of the bone anchor of FIG. 1A, shown with reduction tabs.
Figure 2C:
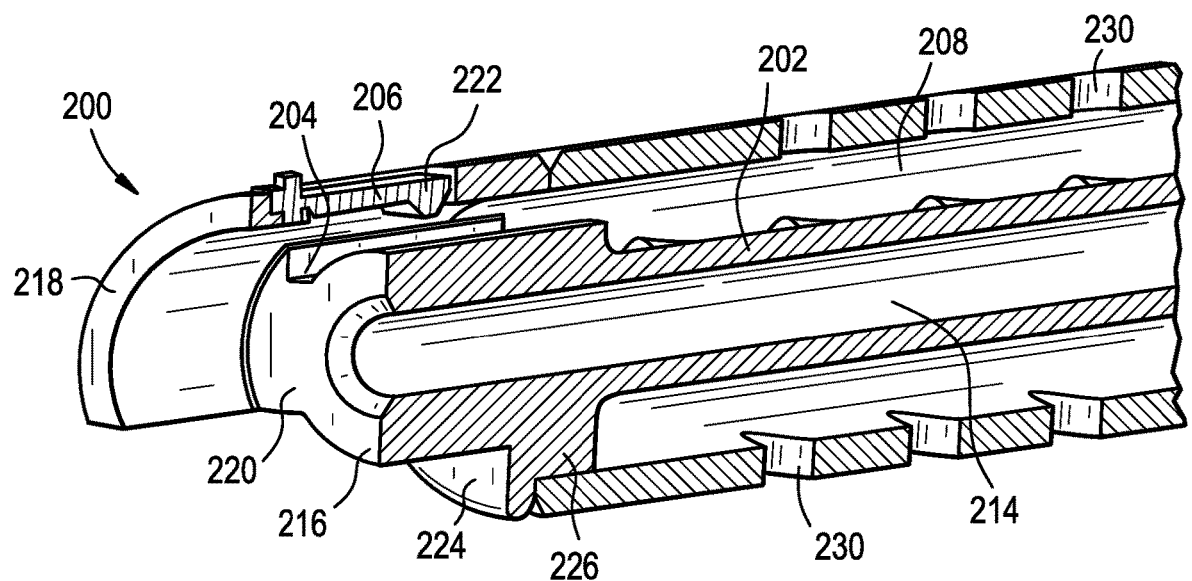
FIG. 2C is a sectional perspective view of the instrument of FIG. 2A.
Figure 2D:
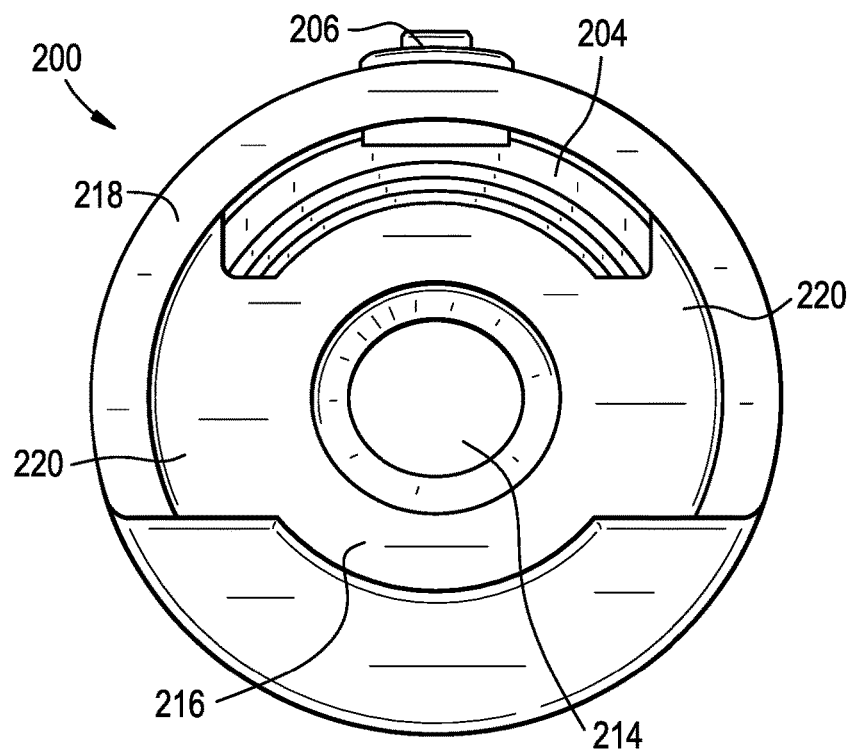
FIG. 2D is an end view of the instrument of FIG. 2A.
Figure 3A:
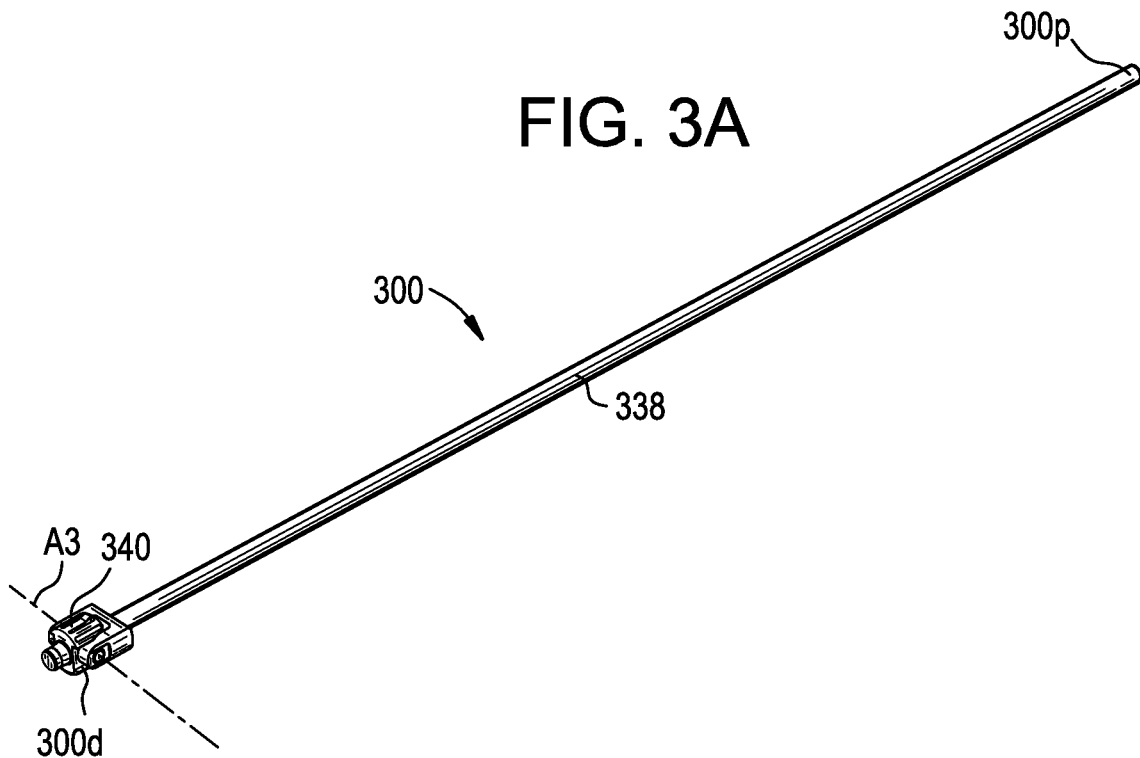
FIG. 3A is a perspective view of a guide rod.
Figure 3B:
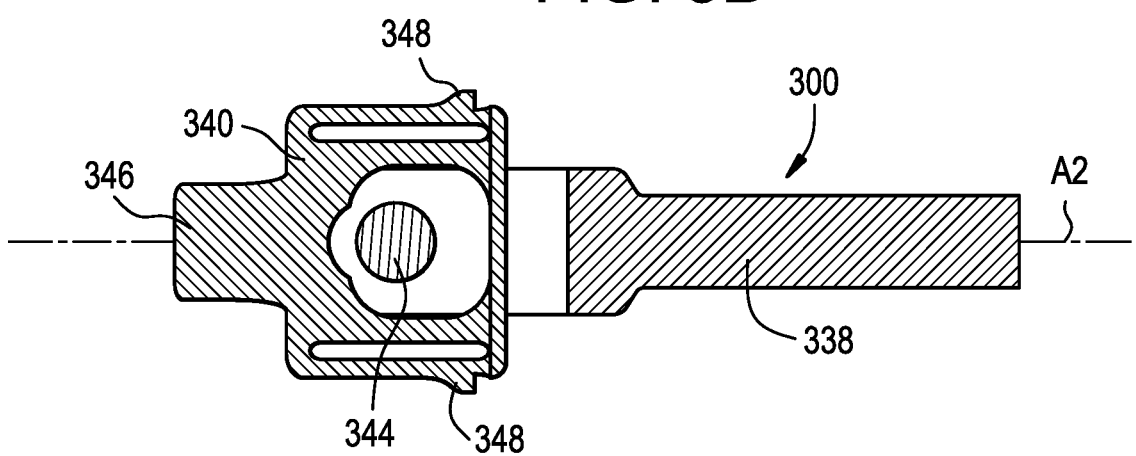
FIG. 3B is a sectional side view of the guide rod of FIG. 3A.
Figure 3C:
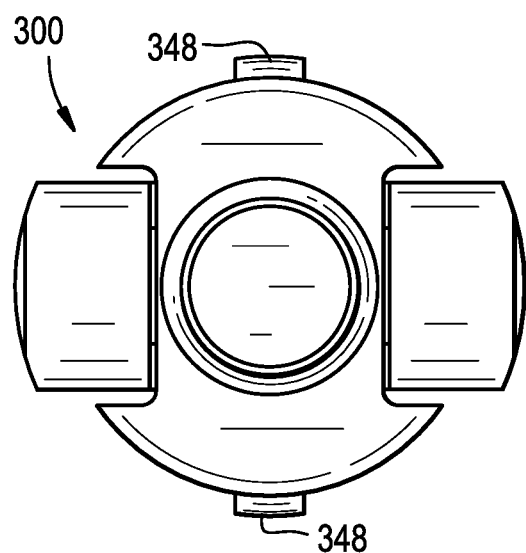
FIG. 3C is an end view of the guide rod of FIG. 3A.
Figure 3D:
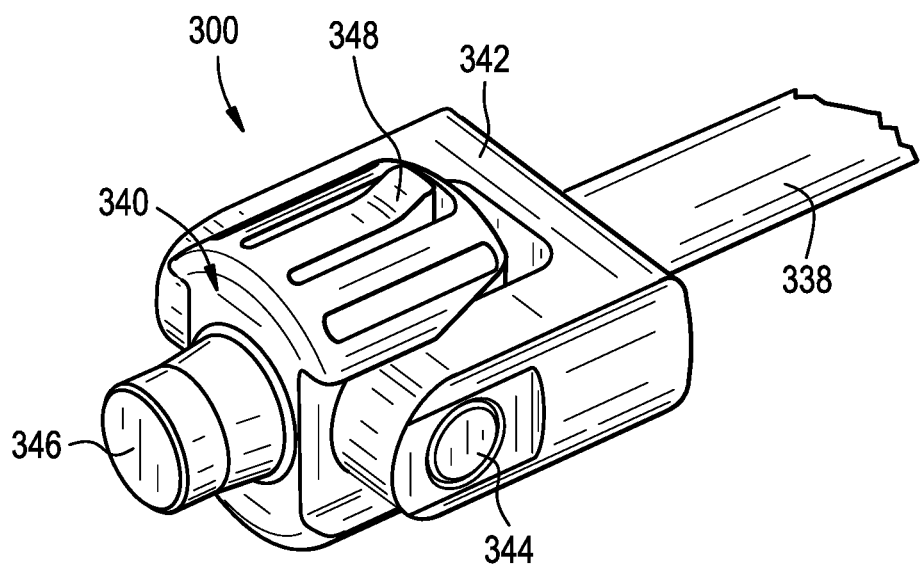
FIG. 3D is another perspective view of the guide rod of FIG. 3A.

FIGS. 1A-1C illustrate a prior art bone anchor 100 with which one or more of the instruments described herein can be used. It will be appreciated that the illustrated bone anchor 100 is exemplary and that the instruments described below can be used with any of a variety of bone anchors.

The illustrated bone anchor 100 includes an anchor portion or shank 102, a head or receiver member 104 for receiving a spinal fixation element, such as a spinal rod 106, to be coupled to the shank 102, and a fastener or closure mechanism 108 to capture a spinal fixation element within the receiver member and fix the spinal fixation element with respect to the receiver member. The shank 102 includes a proximal head 110 and a distal shaft 112 configured to engage bone. The receiver member 104 has a proximal end having a pair of spaced apart arms 114A, 114B defining a recess or channel 116 therebetween and a distal end having a distal end surface defining an opening through which at least a portion of the shank 102 extends. The closure mechanism 108 can be positionable between and can engage the arms 114A, 114B to capture a spinal fixation element, e.g., a spinal rod 106, within the receiver member 104 and fix the spinal fixation element with respect to the receiver member.

The proximal head 110 of the shank 102 is generally in the shape of a truncated sphere having a planar proximal surface and an approximately spherically-shaped distal surface. The illustrated bone anchor 100 is a polyaxial bone screw designed for posterior implantation in the pedicle or lateral mass of a vertebra. The proximal head 110 of the shank 102 engages the distal end of the receiver member 104 in a ball and socket like arrangement in which the proximal head and the distal shaft 112 can pivot relative to the receiver member. The distal surface of the proximal head 110 of the shank 102 and a mating surface within the distal end of the receiver member 104 can have any shape that facilitates this arrangement, including, for example, spherical (as illustrated), toroidal, conical, frustoconical, and any combinations of these shapes.

The distal shaft 112 of the shank 102 can be configured to engage bone and, in the illustrated embodiment, includes an external bone engaging thread. The distal shaft 112 can also include other structures for engaging bone, including a hook. The distal shaft 112 of the shank 102 can be cannulated, having a central passage or cannula extending the length of the shank to facilitate delivery of the shank over a guidewire in, for example, minimally-invasive procedures. Other components of the bone anchor 100, including, for example, the closure mechanism 108, the receiver member 104, and the compression member or cap 118 (discussed below) can be cannulated or otherwise have an opening to permit delivery over a guidewire.

The proximal end of the receiver member 104 includes a pair of spaced apart arms 114A, 114B defining a U-shaped recess 116 therebetween for receiving a spinal fixation element, e.g., a spinal rod 106. Each of the arms 114A, 114B can extend from the distal end of the receiver member 104 to a free end. The outer surfaces of each of the arms 114A, 114B can include a feature, such as a recess, dimple, notch, projection, or the like, to facilitate connection of the receiver member 104 to instruments. For example, the outer surface of each arm 114A, 114B can include an arcuate groove at the respective free end of the arms. Such grooves are described in more detail in U.S. Pat. No. 7,179,261, issued on Feb. 20, 2007, which is hereby incorporated by reference herein.

The distal end of the receiver member 104 includes a distal end surface which is generally annular in shape defining a circular opening through which at least a portion of the shank 102 extends. For example, the distal shaft 112 of the shank 102 can extend through the opening.

The shank 102 can be selectively fixed relative to the receiver member 104. Prior to fixation, the shank 102 is movable relative to the receiver member 104 within a cone of angulation generally defined by the geometry of the distal end of the receiver member and the proximal head 110 of the shank 102. The bone anchor 100 can be a favored angle screw, for example as disclosed in U.S. Pat. No. 6,974,460, issued on Dec. 13, 2005, and in U.S. Pat. No. 6,736,820, issued on May 18, 2004, both of which are hereby incorporated by reference herein. Alternatively, the bone anchor 100 can be a conventional (non-biased) polyaxial screw in which the shank 102 pivots in the same amount in every direction.

The spinal fixation element, e.g., the spinal rod 106, can either directly contact the proximal head 110 of the shank 102 or can contact an intermediate element, e.g., a compression member 118. The compression member 118 can be positioned within the receiver member 104 and interposed between the spinal rod 106 and the proximal head 110 of the shank 102 to compress the distal outer surface of the proximal head into direct, fixed engagement with the distal inner surface of the receiver member 104. The compression member 118 can include a pair of spaced apart arms 120A and 120B defining a U-shaped seat 122 for receiving the spinal rod 106 and a distal surface for engaging the proximal head 110 of the shank 102.

The proximal end of the receiver member 104 can be configured to receive a closure mechanism 108 positionable between and engaging the arms 114A, 114B of the receiver member. The closure mechanism 108 can be configured to capture a spinal fixation element, e.g., a spinal rod 106, within the receiver member 104, to fix the spinal rod relative to the receiver member, and to fix the shank 102 relative to the receiver member. The closure mechanism 108 can be a single set screw having an outer thread for engaging an inner thread provided on the arms 114A, 114B of the receiver member 104. In the illustrated embodiment, however, the closure mechanism 108 includes an outer set screw 124 operable to act on the compression member 118 and an inner set screw 126 operable to act on the rod 106. Various other closure mechanisms 108 can be used instead or in addition, such as a nut that extends around an outer circumference of the receiver member 104, a cap or fastener that slides onto the receiver member from the side, or a cap or fastener that locks to the receiver member by quarter-turn rotation.

The receiver member 104 can include, can be formed integrally with, or can be coupled to one or more reduction tabs or extension tabs 128 (shown in FIG. 1C) that extend proximally from the receiver member 104 to functionally extend the length of the arms 114A, 114B. The reduction tabs 128 can facilitate installation and assembly of a fixation or stabilization construct and can be removed prior to completing a surgical procedure, e.g., using instruments of the type described herein.

The bone anchor 100 can be used with a spinal fixation element such as rigid spinal rod 106. Alternatively, the spinal fixation element can be a dynamic stabilization member that allows controlled mobility between the instrumented vertebrae.

In use, the bone anchor 100 can be assembled such that the distal shaft 112 extends through the opening in the distal end of the receiver member 104 and the proximal head 110 of the shank 102 is received in the distal end of the receiver member 104. A driver instrument can be fitted with the shank 102 to drive the shank into bone. The compression member 118 can be positioned within the receiver member 104 such that the arms 120A, 120B of the compression member are aligned with the arms 114A, 114B of the receiver member 104 and the lower surface of the compression member 118 is in contact with the proximal head 110 of the shank 102. A spinal fixation element, e.g., the spinal rod 106, can be located in the recess 116 of the receiver member 104. The closure mechanism 108 can be engaged with the inner thread provided on the arms 114A, 114B of the receiver member 104. A torsional force can be applied to the outer set screw 124 to move it within the recess 116 so as to force the compression member 118 onto the proximal head 110 of the shank 102, thereby locking the angular position of the shank 102 relative to the receiver member 104. A torsional force can be applied to the inner set screw 126 to force the spinal rod 106 into engagement with the compression member 118 and thereby fix the spinal rod 106 relative to the receiver member 104. In arrangements with a single set screw, a torsional force can be applied to the set screw both to lock the angular position of the shank 102 relative to the receiver member 104 and to fix the spinal rod 106 relative to the receiver member 104.

The instruments disclosed herein can be configured to operate in conjunction with bone anchors of the type described above or various other types known in the art. Exemplary bone anchors with which the instruments disclosed herein can be used include monoaxial screws, polyaxial screws, uniplanar screws, and favored-angle screws.

Instruments and Related Methods for Breaking Reduction Tabs

FIGS. 2A-2D illustrate an exemplary embodiment of an instrument 200 that can be used, for example, to break off a reduction tab from a bone anchor. As shown, the instrument 200 can include an elongate shaft 202 having a distal opening or slot 204 configured to receive a reduction tab. In use, a reduction tab that is attached to a bone anchor can be inserted into the opening 204 and the shaft 202 can be manipulated to break off the reduction tab from the bone anchor, e.g., by rotating or angling the shaft relative to the bone anchor. A retention element 206 can be disposed in association with the opening 204 to help retain the broken off reduction tab within the instrument 200. The instrument 200 can include a chamber 208 in which one or more broken off reduction tabs can be captured and stored. For example, the chamber 208 can be defined between an outer surface of the shaft 202 and an inner surface of a sleeve 210 concentrically disposed around the shaft. A cap 212 can be attached at a proximal portion of the shaft 202. The cap 212 can help retain the outer sleeve 210 to the shaft 202 and/or can be removable to access or to empty the chamber 208. The shaft 202 can define an inner lumen or cannulation 214 to facilitate use of the instrument 200 over a guidewire or over a guide rod of the type described herein. The cap 212 can include a cannulation that is coaxial with the cannulation 214.

The shaft 202 can include an elongate body 216 having a proximal end 216p and a distal end 216d and extending along a central longitudinal axis A1. The body 216 can be generally cylindrical. The body 216 can be solid or, as shown, can be cannulated to allow passage of a guidewire or guide rod therethrough.

The opening 204 for receiving a reduction tab can be defined by a distal portion of the shaft 202. For example, the opening 204 can be defined by a clearance space between an outer surface of the body 216 and an inner surface of a shroud 218. The shroud 218 can be integrally or monolithically formed with the body 216, or can be a separate component attached thereto. The shroud 218 can be a partial or complete cylindrical tube. The inside diameter of the shroud 218 can be greater than an outside diameter of the shaft body 216 such that a clearance space is formed therebetween to define the opening 204. The difference between the inside diameter of the shroud 218 and the outside diameter of the body 216 can be selected to define the radial dimension of the opening 204. The opening 204 can have a radial dimension that is equal to or slightly greater than the radial thickness of a reduction tab with which the instrument 200 is to be used. Alternatively, the radial dimension of the opening 204 can be slightly less than the thickness of the reduction tab, to form an interference fit when the tab is inserted into the opening.

The shroud 218 can be connected to the body 216, and can be supported in a spaced relationship from the body, by one or more struts 220. The struts 220 can extend radially-outward from the body 216 to the shroud 218. In the illustrated example, the body 216 includes first and second diametrically-opposed struts 220 that extend from an outer surface of the body to the inner surface of the shroud 218. The positioning of the struts 220 and the circumferential width of the struts can be selected to define the circumferential dimension of the opening 204. The opening 204 can have a circumferential dimension that is equal to or slightly greater than the width of a reduction tab with which the instrument 200 is to be used. Alternatively, the circumferential dimension of the opening 204 can be slightly less than the width of the reduction tab, to form an interference fit when the tab is inserted into the opening.

The illustrated opening 204 is formed generally as a negative of a section of a tube. While such an opening is shown and described herein, it will be appreciated that the geometry of the opening 204 can vary depending on the shape and size of the reduction tabs with which the instrument 200 is to be used. The opening 204 can have a cross section in a plane transverse to the axis A1 that is the same as or substantially the same as a corresponding cross section of the reduction tab.

The shroud 218 can have a cylindrical or substantially cylindrical exterior surface. The outside diameter of the shroud 218 can be less than or equal to the outside diameter of the outer sleeve 210. The outside diameter of the shroud 218 can be less than or equal to the diameter of a percutaneous or minimally-invasive working channel in which a bone anchor to be used with the instrument 200 is disposed. The inside diameter of the shroud 218 can be equal to or only slightly greater than a maximum outside diameter of the reduction tabs of a bone anchor with which the instrument 200 is to be used. When a reduction tab of a bone anchor is inserted into the opening 204, the axis A1 of the shaft 202 can be collinear with a central longitudinal axis of the head or receiver member of the bone anchor.

A retention element 206 can be disposed in association with the opening 204 to help retain a broken off reduction tab within the instrument 200. For example, the instrument 200 can include a biased finger 206 configured to interfere with a reduction tab inserted into the opening 204 to exert a frictional force on the reduction tab. The finger 206 can be formed as cantilevered beam with a contact tip 222 that projects radially-inward from the beam.

The finger or other retention element 206 can be attached to, or can be formed integrally with, any one or more of the shroud 218, the body 216, and the sleeve 210. The retention element 206 can be attached by welding, adhesives, or other fasteners, such as a through-pin as shown. While a single retention element 206 attached to the shroud 218 is shown, the instrument can include a plurality of retention elements. For example, the shroud 218 can include a first retention element and the body 216 can include a second retention element such that the retention elements are positioned on opposites sides of the opening 204. Various other types of retention elements can be used instead or in addition, such as a ball plunger, a leaf spring, a coil spring, ratchet teeth, surface coatings or features, and the like.

The distal end of the shaft 202 can include a radial flange 224. The flange 224 can define a proximal-facing shoulder against which the outer sleeve 210 can abut to capture and retain the sleeve between the flange and the cap 212. The flange 224 can include a cylindrical boss 226 sized to be received within the distal end of the sleeve 210 to center the sleeve coaxially with the shaft 202.

The proximal end of the shaft 202 can include a mating feature 228 for securing the cap 212 to the instrument 200. For example, as shown, the proximal end of the shaft 202 can include an exterior thread 228 configured to mate with an interior thread of the cap 212. While a threaded coupling is shown, it will be appreciated that various other attachment mechanisms can be used instead or in addition, such as a bayonet coupling, a snap-fit or interference coupling, etc.

The sleeve 210 can be formed as an elongate cylindrical tube. The inside diameter of the sleeve 210 can be greater than an outside diameter of the body 216 of the shaft 202, such that a clearance space is formed therebetween to define the chamber 208. The length and volume of the chamber 208 can be selected to fit one or more broken-off reduction tabs therein. In some embodiments, the chamber 208 can be sized to hold a plurality of reduction tabs simultaneously. The sidewall of the sleeve 210 can be solid or can include one or more openings 230 therein. The openings 230 can allow visibility into the chamber 208, e.g., to allow a user to assess the number of reduction tabs in the chamber or the inserted depth of a reduction tab into the chamber. The openings 230 can also facilitate cleaning and sterilization of the instrument 200 by allowing a fluid to easily flow into and out of the chamber 208 during such processes.

The cap 212 can define a distal-facing shoulder 232 against which the outer sleeve 210 can abut to capture and retain the sleeve between the flange 224 of the shaft 202 and the cap. The cap 212 can include a tubular boss 234 sized to be received within the proximal end of the sleeve 210 to center the sleeve coaxially with the shaft 202. The cap 212 can include a mating feature 236 for securing the cap to the instrument 200. For example, as described above, the cap 212 can include an interior thread 236 configured to mate with an exterior thread 228 of the shaft 202. An outer surface of the cap 212 can include gripping features to facilitate application of torque to the cap by the user, e.g., to tighten or loosen the cap from the instrument 200.

In some embodiments, the cap 212 can be formed integrally with the sleeve 210 or the shaft 202. In some embodiments, the sleeve 210 can be formed integrally with the shaft 202. In some embodiments, the cap 212 and/or the sleeve 210 can be omitted.

Exemplary instruments for breaking reduction tabs are disclosed in U.S. Pat. No. 9,402,673 of Cormier et al., entitled DEVICES AND METHODS FOR BREAKING AND RETAINING SURGICAL REDUCTION TABS, which is hereby incorporated by reference herein. The instrument 200 can include any of the features or variations described in the above reference.

FIGS. 3A-3D illustrate an exemplary guide rod 300 that can be used with any of the tab breaker instruments described herein, e.g., the instrument 200 described above. The guide rod 300 can include a distal portion configured to be secured or docked to an implanted bone anchor and a proximal guide portion over which an instrument can be advanced into proximity to the bone anchor. The guide rod 300 can be particularly useful in percutaneous or minimally-invasive procedures in which it may be difficult to visualize the implanted bone anchor and to align a reduction tab of the bone anchor with the opening of a tab breaker instrument.

The guide rod 300 can include proximal and distal ends 300p, 300d that define a central longitudinal axis A2 therebetween. The guide rod 300 can include an elongate guide shaft 338 and a distal plug 340. The guide shaft 338 can be cylindrical and can be sized to be received within a cannulation of an instrument, e.g., the cannulation 214 of the instrument 200 described above.

The distal plug 340 can be movably coupled to the guide shaft 338. For example, the distal plug 340 can be rotatable relative to the guide shaft 338 about an axis A3 that is perpendicular to the axis A2. In the illustrated embodiment, the plug 340 is received between first and second arms of a clevis 342 formed at the distal end of the guide shaft 338. A hinge pin 344 can extend through the arms and the plug 340 and can be rotatable with respect to the plug and/or the arms such that the plug can rotate about the axis A3 relative to the guide shaft 338. In some embodiments, one or more of the openings in which the hinge pin 344 is disposed (e.g., the openings in the arms and/or the opening in the plug 340) can be oversized relative to the hinge pin to allow some amount of play, which can facilitate translating movement of the guide shaft 338 relative to the plug 340. For example, a small amount of translation along the axis A1 and perpendicular to the axis A1 can be permitted between the guide shaft 338 and the plug 340.

The plug 340 can include features for aligning the plug with a bone anchor. For example, the plug 340 can include a distal projection 346 sized to fit within the drive recess of the shank of the bone anchor and/or within the drive recess of a set screw or other fastener coupled to the bone anchor.

The plug 340 can include features for securing the guide rod 300 to a bone anchor. For example, the plug 340 can include one or more radial projections 348 configured to engage with corresponding features of the bone anchor, e.g., internal threads of the reduction tabs or of the receiver head of the bone anchor. The projections 348 can click, snap, or thread into engagement with the threads of the bone anchor to resist or prevent withdrawal of the plug 340 from the bone anchor. The illustrated projections 348 are formed as cantilevered spring arms, though it will be appreciated that various other arrangements can be used instead or in addition. While two projections 348 spaced 90 degrees apart from the hinge pin 344 ends are shown, the plug 340 can include any number of projections at any desired spacing.

Figure 4A:
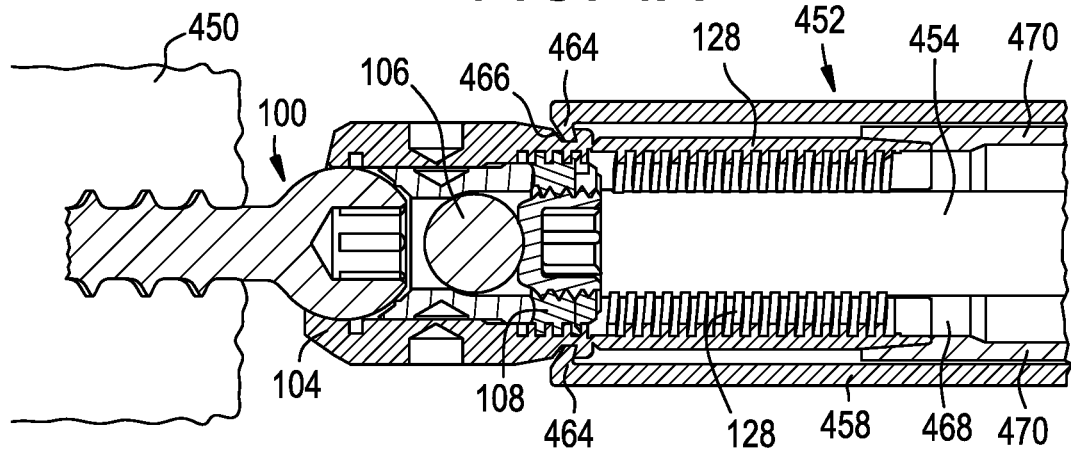
FIG. 4A is a sectional side view of a bone anchor with an access device attached thereto.
Figure 4B:
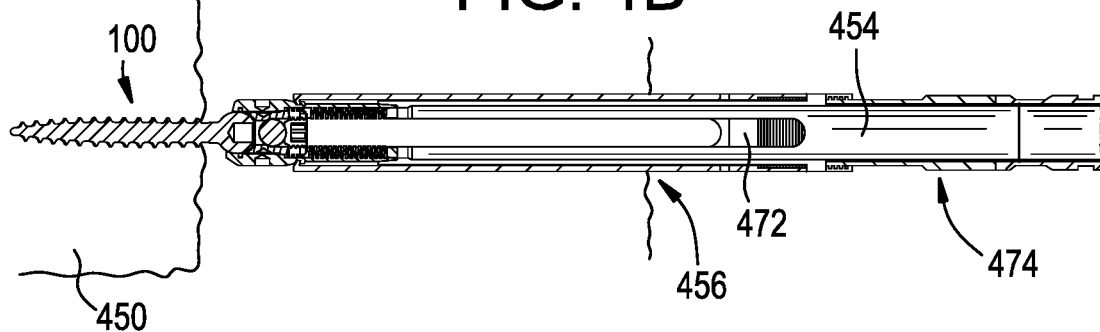
FIG. 4B is another sectional side view of the bone anchor and access device of FIG. 4A.
Figure 4C:
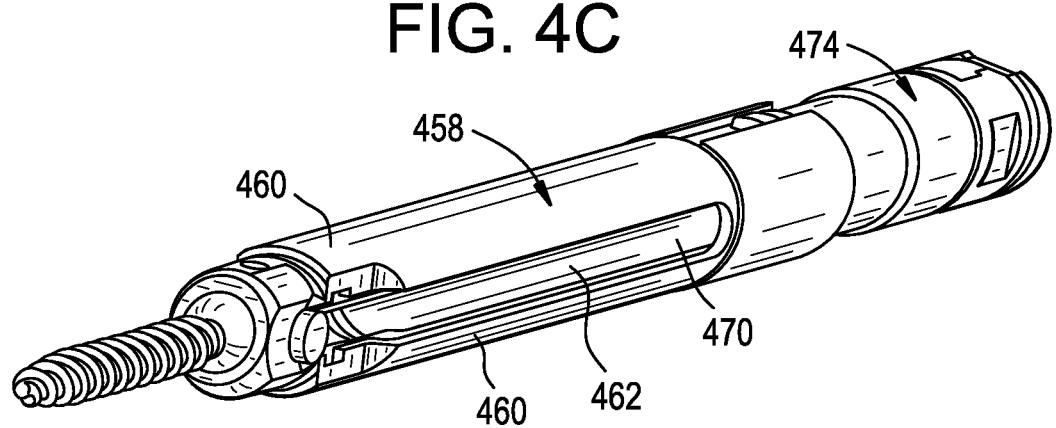
FIG. 4C is a perspective view of the bone anchor and access device of FIG. 4A.
Figure 4D:
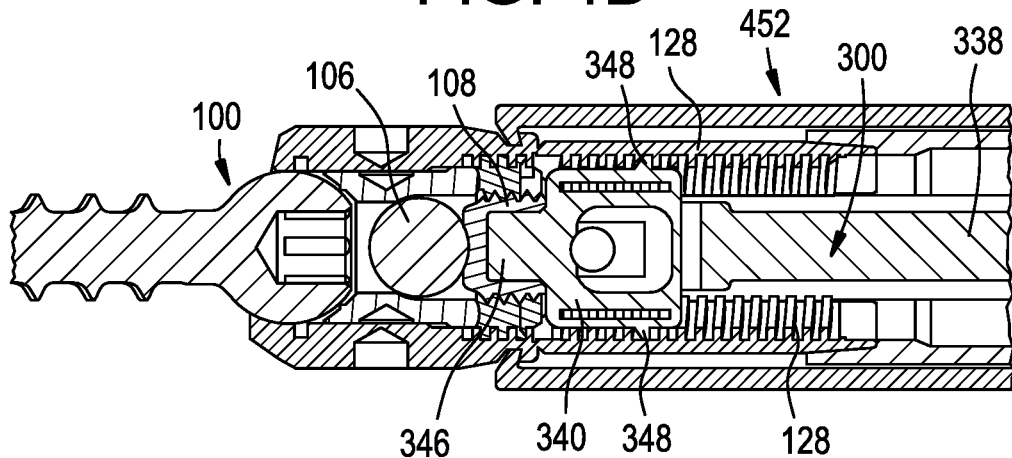
FIG. 4D is a sectional side view of the bone anchor and access device of FIG. 4A with the guide rod of FIG. 3A inserted through the access device.
Figure 4E:
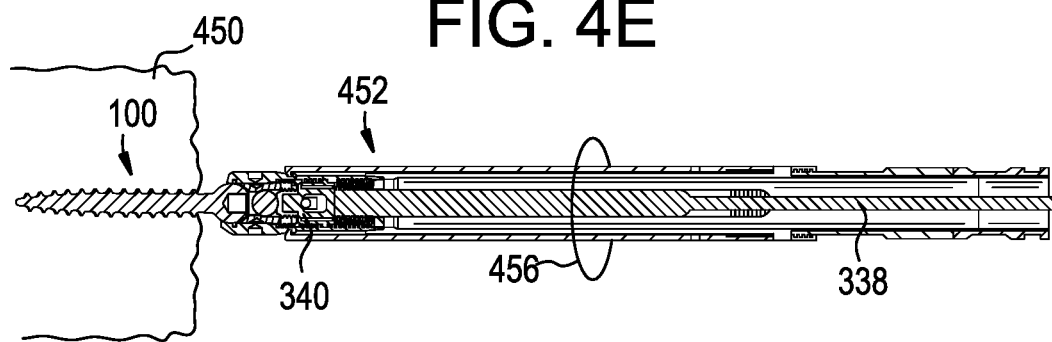
FIG. 4E is another sectional side view of the bone anchor, access device, and guide rod of FIG. 4D.
Figure 4F:
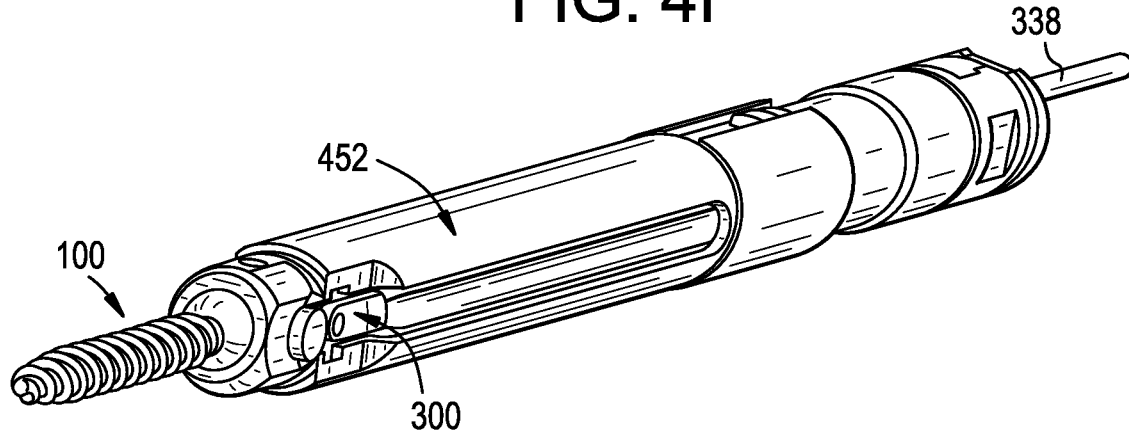
FIG. 4F is a perspective view of the bone anchor, access device, and guide rod of FIG. 4D.
Figure 4G:
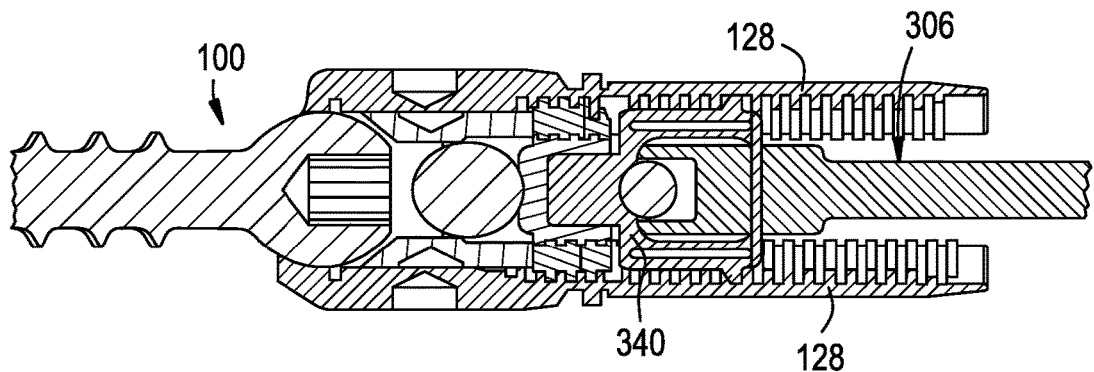
FIG. 4G is a sectional side view of the bone anchor and guide rod of FIG. 4D with the access device removed.
Figure 4H:
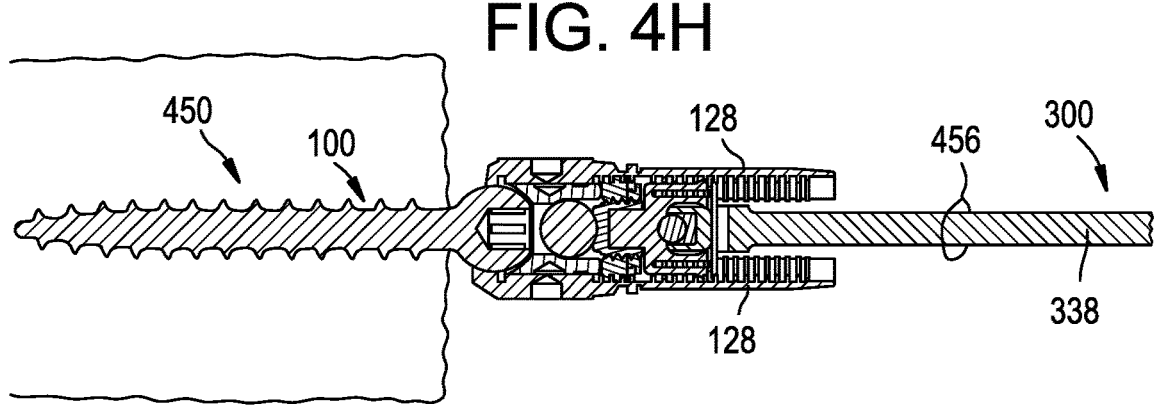
FIG. 4H is another sectional side view of the bone anchor and guide rod of FIG. 4G.
Figure 4I:
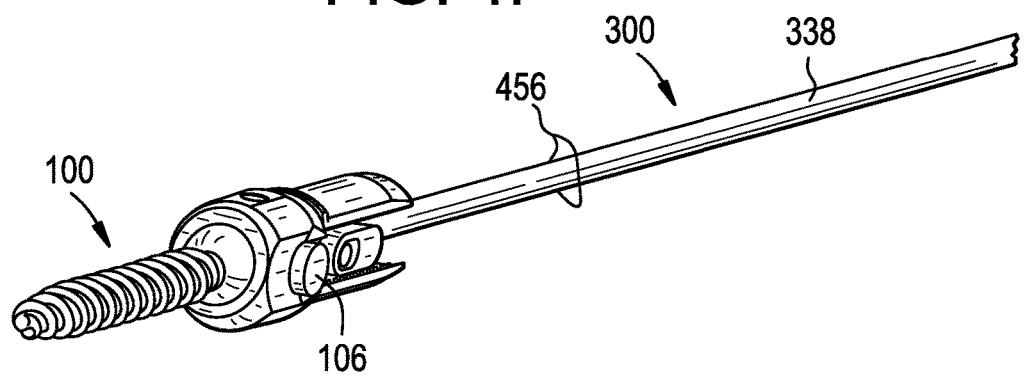
FIG. 4I is a perspective view of the bone anchor and guide rod of FIG. 4G.
Figure 4J:
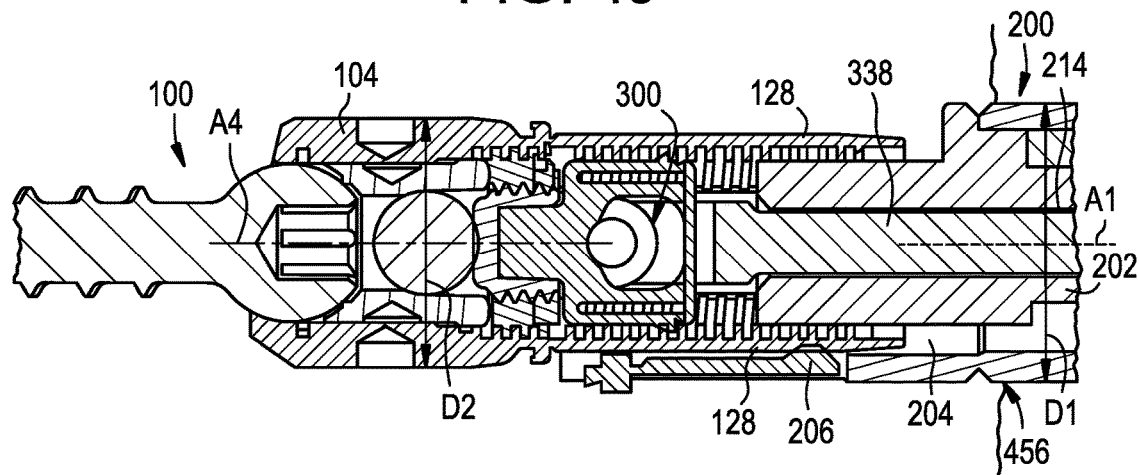
FIG. 4J is a sectional side view of the bone anchor and guide rod of FIG. 4G with an extension tab of the bone anchor received in the instrument of FIG. 2A.
Figure 4K:
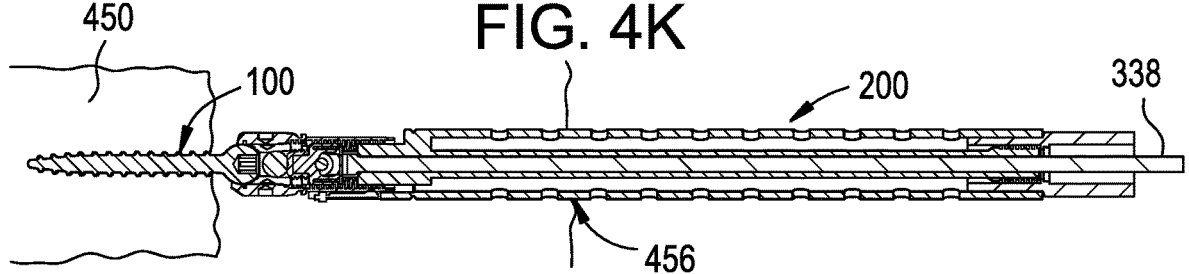
FIG. 4K is another sectional side view of the bone anchor, guide rod, and instrument of FIG. 4J.
Figure 4L:
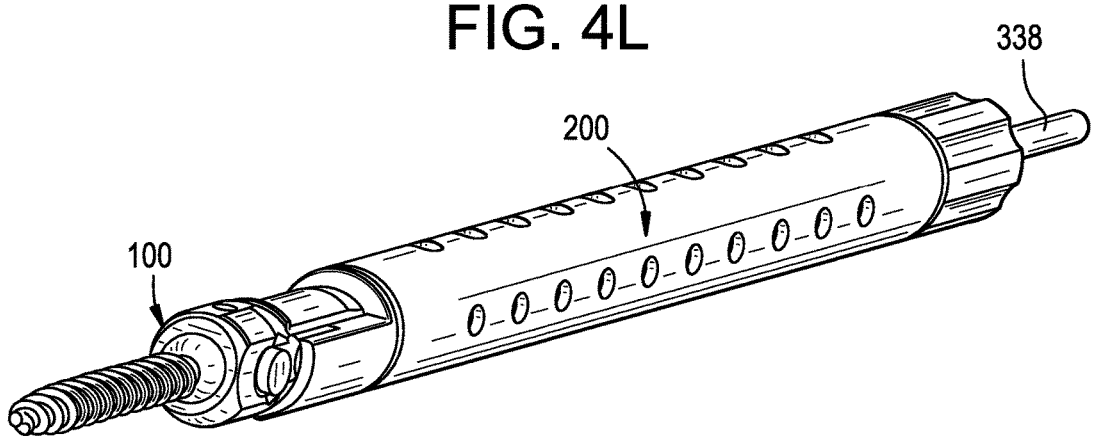
FIG. 4L is a perspective view of the bone anchor, guide rod, and instrument of FIG. 4J.
Figure 4M:
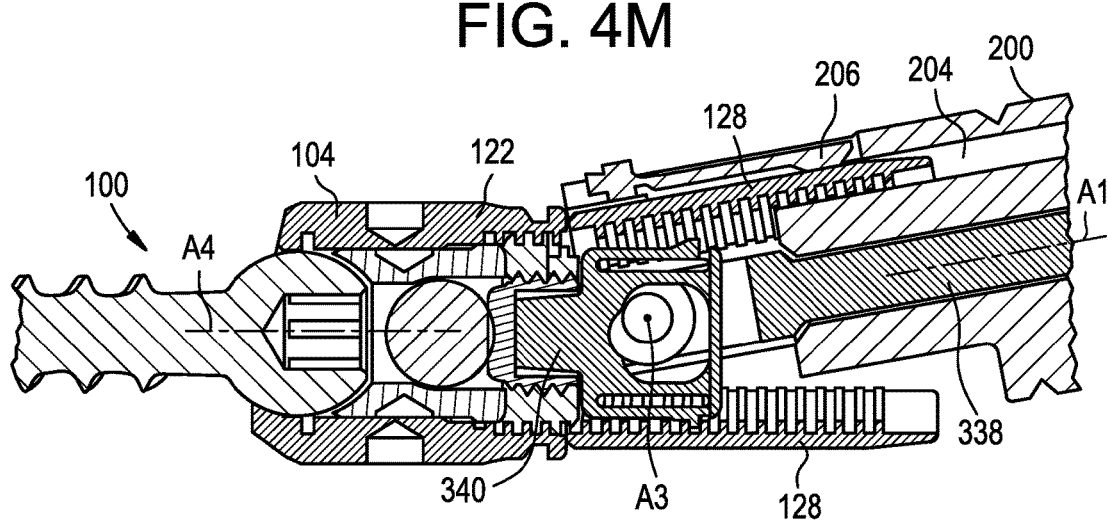
FIG. 4M is a sectional side view of the bone anchor, guide rod, and instrument of FIG. 4J, with the instrument manipulated to break the reduction tab.
Figure 4N:
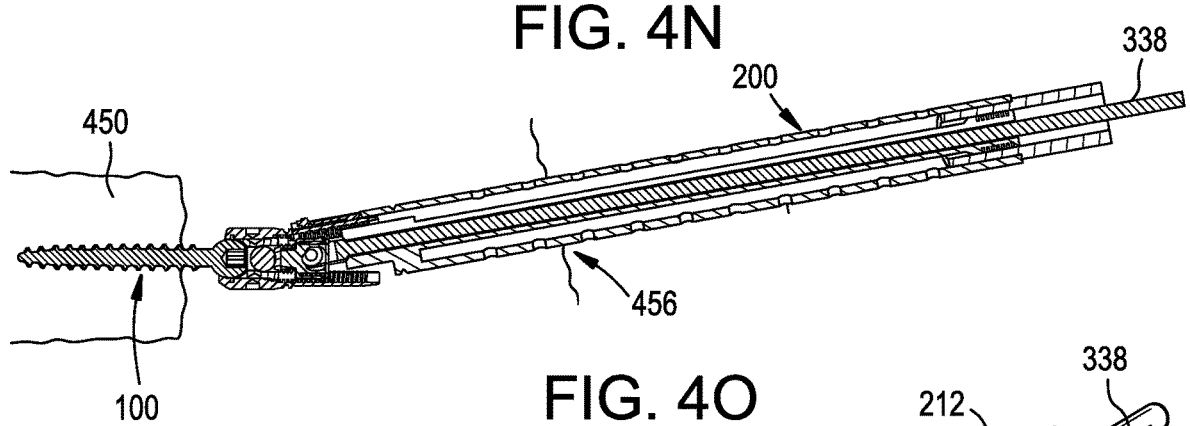
FIG. 4N is another sectional side view of the bone anchor, guide rod, and instrument of FIG. 4M.
Figure 4O:
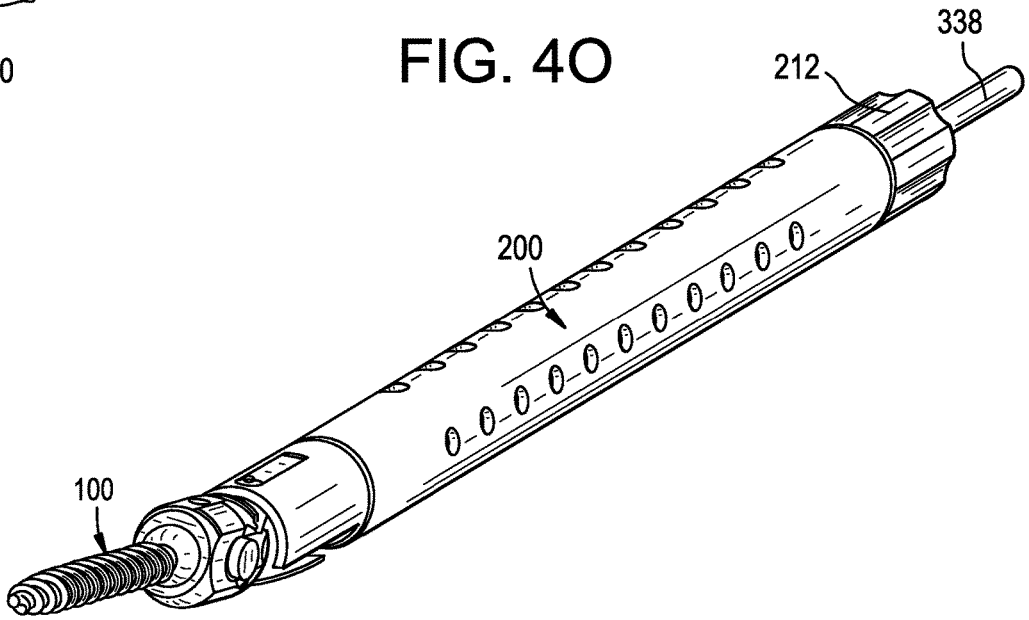
FIG. 4O is a perspective view of the bone anchor, guide rod, and instrument of FIG. 4M.
Figure 5A:
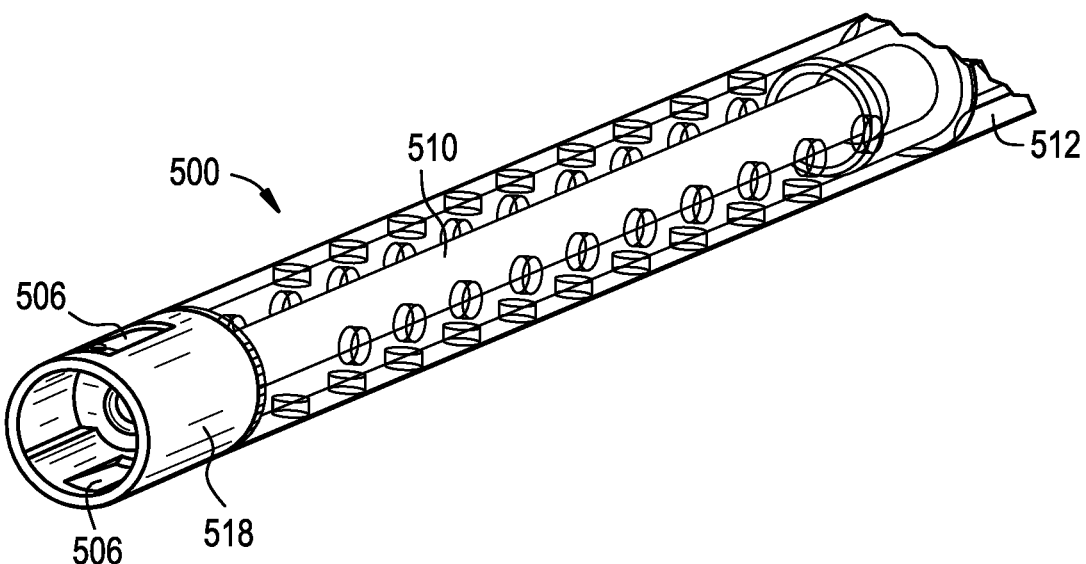
FIG. 5A is a perspective view of an instrument that can be used to break reduction tabs.
Figure 5B:
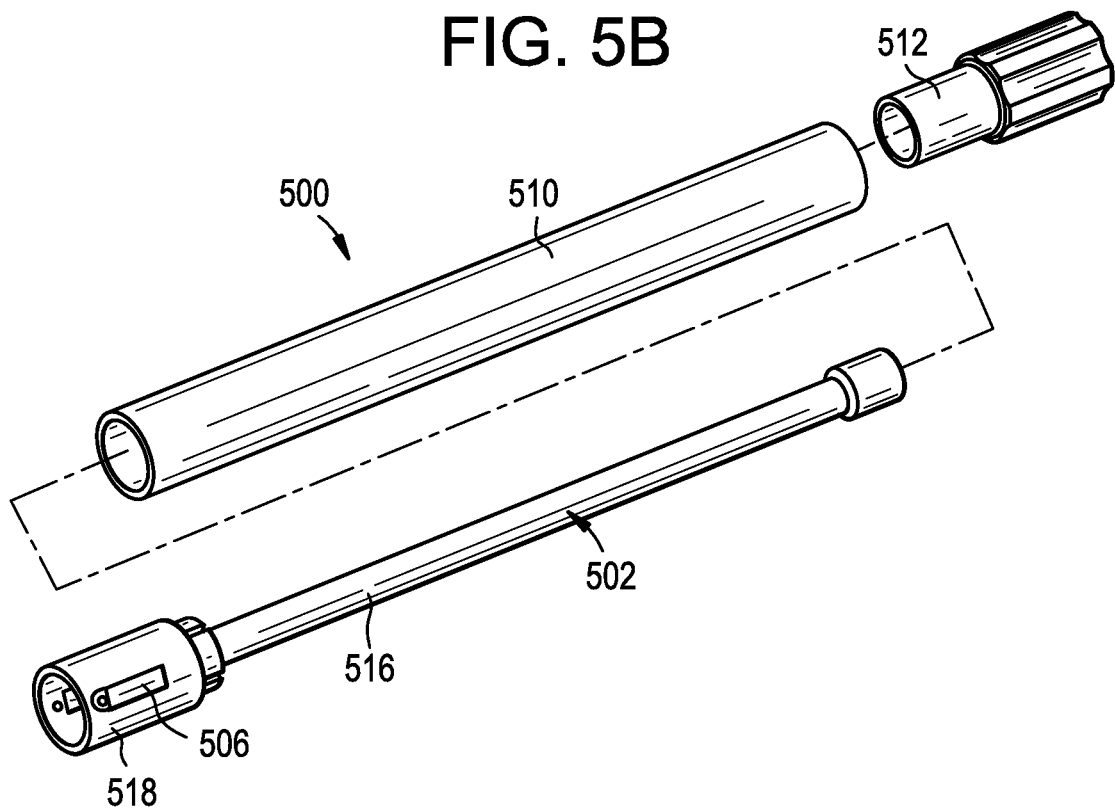
FIG. 5B is an exploded perspective view of the instrument of FIG. 5A.
Figure 5C:
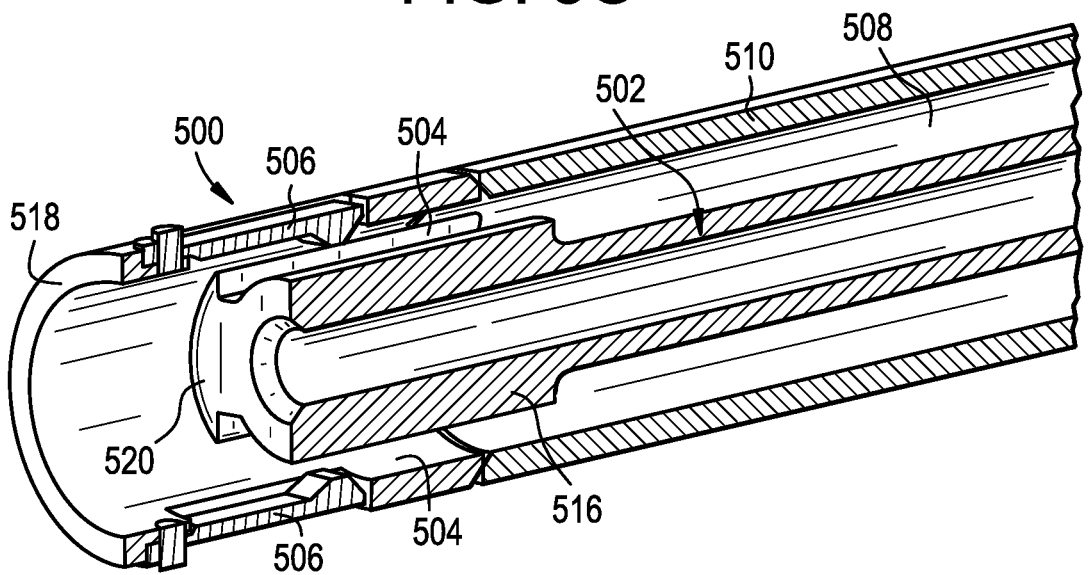
FIG. 5C is a sectional perspective view of the instrument of FIG. 5A.
Figure 5D:
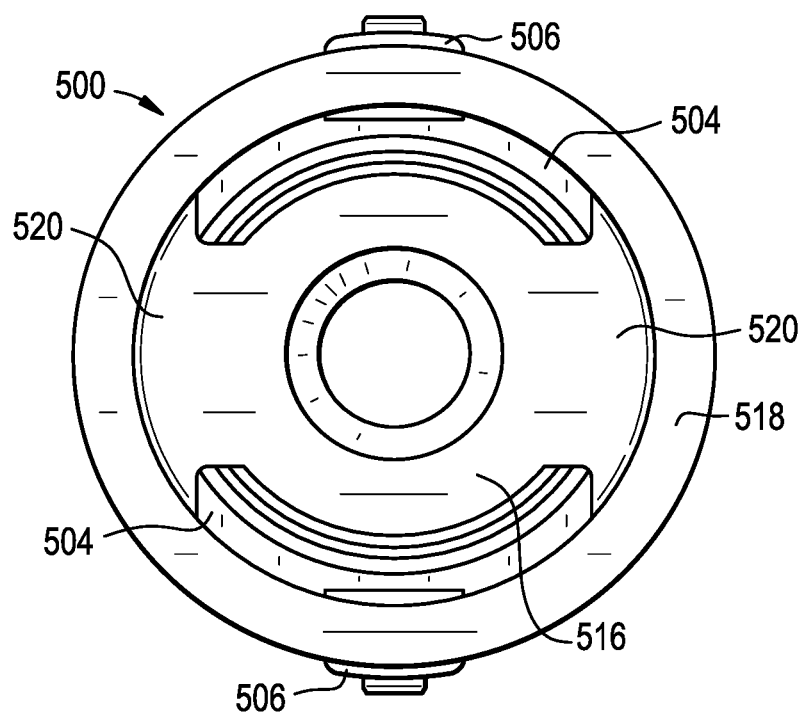
FIG. 5D is an end view of the instrument of FIG. 5A.

An exemplary method of using the instrument 200 is shown in FIGS. 4A-4O. As shown in FIGS. 4A-4C, a bone anchor 100 having one or more reduction tabs 128 can be driven into a bone 450 of a patient, e.g., a pedicle or lateral mass of a patient's vertebra. Using known techniques, a rod or other fixation element 106 can be seated in the bone anchor 100, and a fastener 108 can be applied to the bone anchor to retain the rod therein. The reduction tabs 128 can be used to facilitate the above steps. For example, a threaded reduction instrument (not shown) can be advanced along internal threads of the reduction tabs 128 to bear against the rod 106 and urge the rod distally into the recess of the bone anchor 100. As another example, the fastener 108 can be engaged with the threads of the reduction tabs 128 and rotated to advance the fastener and the rod 106 distally, urging the rod towards the recess of the bone anchor 100 and eventually moving the fastener into the threads of the bone anchor receiver 104.

As also shown in FIGS. 4A-4C, an access device 452 can be coupled to the bone anchor 100 to establish a working channel 454 between the bone anchor and a skin incision 456. The access device 452 can be attached to the bone anchor 100 before or after driving the bone anchor into the bone 450, and before or after seating the rod 106 and fastener 108 in the bone anchor. Exemplary access devices are disclosed in U.S. Pat. No. 7,179,261 of Sicvol et al., entitled PERCUTANEOUS ACCESS DEVICES AND BONE ANCHOR ASSEMBLIES, which is hereby incorporated by reference herein.

The illustrated access device 452 includes an outer sleeve 458 with opposed arms 460 that define a rod channel 462 therebetween. The arms 460 include projections 464 configured to be received within corresponding grooves 466 formed in the exterior surface of the arms of the receiver 104 of the bone anchor 100 to retain the outer sleeve 458 to the bone anchor. The access device 452 also includes an inner sleeve 468 configured to translate longitudinally relative to the outer sleeve 458. The inner sleeve 468 can be advanced distally relative to the outer sleeve 458 and can bear against the proximal ends of the extension tabs 128. For example, the inner sleeve 468 can include a distal-facing ramped surface that forms a negative of and bears against a proximal-facing ramped surface of the extension tabs 128. The inner sleeve 468 can include an inwardly-projecting shoulder that contacts and bears against the proximal ends of the reduction tabs 128. Urging the inner sleeve 468 distally can cause the outer sleeve 458 to be pulled proximally into firm engagement with the grooves 466 of the bone anchor 100, thereby securing the access device 452 to the bone anchor. The inner sleeve 468 can be translated longitudinally relative to the outer sleeve 458 without rotating relative to the outer sleeve, such that opposed arms 470 of the inner sleeve remain aligned with the opposed arms 460 of the outer sleeve and such that a rod channel 472 of the inner sleeve remains aligned with the rod channel 462 of the outer sleeve and the rod channel of the bone anchor 100. A pusher sleeve 474 can be threadably coupled to the outer sleeve 458 and can bear against a proximal end of the inner sleeve 468. Rotation of the pusher sleeve 474 relative to the outer sleeve 458 can cause the pusher sleeve to translate longitudinally relative to the outer sleeve and to push the inner sleeve 468 distally without rotating the inner sleeve.

A guidewire or a guide rod can be used to help align the instrument 200 with the reduction tabs 128 of the bone anchor 100. For example, as shown in FIGS. 4D-4F, a guide rod 300 of the type described herein can be inserted through the access device 452 and advanced towards the bone anchor 100. The plug 340 of the guide rod 300 can be advanced distally relative to the bone anchor 100 until the alignment projection 346 of the plug is seated in the drive recess of the fastener 108 of the bone anchor. As the plug 340 is advanced distally, the radial projections 348 of the plug can engage with the interior threads of the reduction tabs 128 to retain the plug to the bone anchor 100. For example, interference can exist between the projections 348 and the threads of the reduction tabs 128, such that the projections and the beams to which they are mounted deflect radially inward as the plug 340 is advanced across each crest of the thread. Once the projection 348 passes the crest, the beam and the projection 348 can spring radially outward to seat the projection in the root of the thread. The distal-facing surface of the projections 348 can be ramped, curved, or otherwise tapered to facilitate deflection of the projections during distal advancement. The proximal-facing surface of the projections 348 can be planar and can extend perpendicular to the axis A2 to resist or prevent proximal retraction of the plug 340. The thread and the projections 348 can thus interlock to secure the plug 340 to the reduction tabs 128 or to the arms of the bone anchor 100.

Once the guide rod 300 is in place, or at any other time desired by the user, the access device 452 can be separated from the bone anchor 100 and removed from the incision 456. As shown in FIGS. 4G-4I, the guide rod 300 can be left in place when the access device 452 is removed, serving as a guide for advancing the instrument 200 into engagement with the reduction tabs 128 of the bone anchor 100.

When the user desires to break off a reduction tab 128 of the bone anchor 100, the instrument 200 can be passed over the guide rod 300 and positioned with respect to the bone anchor as shown in FIGS. 4J-4L. In particular, the guide shaft 338 of the guide rod 300 can be inserted through the cannulation 214 of the inner shaft 202 of the instrument 200. The instrument 200 can then be translated distally along the guide rod 300 to move the distal end of the instrument into the incision 456 and into proximity to the bone anchor 100. The instrument 200 can be further advanced to slide one of the reduction tabs 128 into the opening 204 of the instrument. Insertion of the reduction tab 128 into the opening 204 can cause deflection of the retaining element 206, thereby exerting a frictional force on the reduction tab to help hold the reduction tab within the instrument 200 after it is broken off. The use of a guide rod 300 can thus help automatically align the reduction tab 128 with the opening 204. This can be particularly advantageous when the instrument 200 is used with reduction tabs 128 which are shorter than the depth of the incision 456 in which they are placed (such as the illustrated reduction tabs).

With the instrument 200 positioned as shown, the instrument is ready to be used to break off the reduction tab 128. In this ready position, as shown, the central longitudinal axis A1 of the instrument shaft 202 can be collinear with a central longitudinal axis A4 of the receiver head 104 of the bone anchor 100. This coaxial arrangement of the instrument 200 with the receiver member 104 can advantageously reduce the degree to which tissue around the bone anchor 100 must be cut or retracted to accommodate the instrument 200 during use. This is in contrast with some conventional tab breaker instruments, in which the central longitudinal axis of the tab breaker is laterally offset from the central longitudinal axis of the receiver while in the above-described ready position, requiring additional tissue resection or retraction to the side of the bone anchor to accommodate the instrument. While a coaxial arrangement can be advantageous in some embodiments, in other embodiments the central longitudinal axis A1 of the instrument 200 can be laterally offset from the central longitudinal axis A4 of the receiver 104.

Also in this ready position, the maximum outer transverse dimension D1 of the instrument 200 can be less than the maximum outer transverse dimension D2 of the bone anchor 100, equal to the maximum outer dimension of the bone anchor, or only slightly greater than the maximum outer dimension of the bone anchor. The maximum outer dimension D1 of the instrument 200 can be less than about 15% greater than the maximum outer dimension D2 of the bone anchor 100, less than about 10% greater than the maximum outer dimension of the bone anchor, and/or less than about 5% greater than the maximum outer dimension of the bone anchor. By limiting the dimension D1, the size of the incision 456 can advantageously be kept small, e.g., only as large as needed to insert the bone anchor 100 using a typical percutaneous approach. This is in contrast with some conventional tab breaker instruments, which can have a maximum outer dimension that is significantly greater than a maximum outer dimension of the bone anchor 100. While a reduced dimension D1 can be advantageous in some embodiments, in other embodiments the dimension D1 can be significantly greater than the maximum outer dimension D1 of the bone anchor.

FIGS. 4M-4O illustrate an exemplary manipulation of the instrument 200 to break the reduction tab 128 received within the opening 204. As shown, the instrument 200 can be angled relative to the bone anchor 100 such that the central longitudinal axis A1 of the instrument 200 is obliquely angled with respect to the central longitudinal axis A4 of the bone anchor 100. With the reduction tab 128 captured within the opening 204 of the instrument 200, this movement can cause the reduction tab to bend relative to the arm 122 from which it extends until the reduction tab breaks off from the arm. The plug 340 can rotate and/or translate relative to the guide shaft 338 about the axis A3, allowing the guide shaft to move with the instrument 200 while the plug remains seated in the bone anchor 100. Even with the now-broken reduction tab 128 being separated from the plug 340, the engagement between the plug and the fastener 108 and the engagement between the plug and the remaining reduction tab can be sufficient to keep the plug in place within the bone anchor 100. Once separated from the bone anchor 100, the reduction tab 128 can be held within the opening 204 by the retaining element 206 of the instrument 200. While an outward angling movement is shown, in other examples the instrument 200 can be angled inward to break the tab 128 or rotated about the axis A1 to break the tab.

To break off the remaining reduction tab 128, the instrument 200 can be translated proximally along the guide shaft 338, rotated 180 degrees about its center axis A1, and then translated distally to insert the second reduction tab into the opening 204. The above steps can be repeated to break off the remaining reduction tab 128. Insertion of the second reduction tab 128 into the opening 204 can force a previously-broken reduction tab disposed therein proximally into the chamber 208 where it can be retained and stored. When the chamber 208 is full, or at any other desired time, the cap 212 of the instrument 200 can be removed and the chamber contents can be emptied through the proximal end of the instrument.

Once both reduction tabs 128 are broken off from the bone anchor 100, or at any other desired time, the instrument 200 and the guide rod 300 can be withdrawn proximally from the bone anchor 100 and removed from the surgical site. The surgical procedure can then be completed and the incision closed using known techniques.

FIGS. 5A-5D illustrate an exemplary embodiment of an instrument 500 that can be used, for example, to break off a reduction tab from a bone anchor. Except as indicated below and as will be readily appreciated by a person having ordinary skill in the art having reviewed this disclosure, the structure and function of the instrument 500 is the same as that of the instrument 200, and therefore a detailed description is omitted here for the sake of brevity.

The instrument 500 can include multiple openings for receiving reduction tabs. For example, as shown, the instrument can include first and second diametrically opposed openings 504 configured to receive reduction tabs therein. The openings 504 can be sized and positioned such that first and second opposed reduction tabs attached to a bone anchor can be simultaneously positioned in the first and second openings, respectively. Each of the openings 504 of the instrument can include one or more associated retention elements 506. While two openings 504 and two retention elements 506 are shown, it will be appreciated that the instrument 500 can include any number of openings and any number of retention elements. The shroud 518 of the instrument 500 can be a complete cylindrical tube. The shroud 518 can be supported in a spaced apart position from the body 516 of the shaft 502 by one or more struts 520. The outer sleeve 510 of the chamber 508 can bear against a proximal end surface of the shroud 518. Both of the openings 504 can empty into the same chamber 508, or the chamber can have internal baffles or dividers to define independent chambers for each opening.

The instrument 500 can be used in the same manner as described above with respect to the instrument 200, except that the instrument 500 can be configured to break multiple reduction tabs of a bone anchor in a single movement. For example, a single angling or rotating manipulation of the instrument 500 relative to the bone anchor 100 can be effective to break both reduction tabs 128 of the bone anchor. If a single motion is insufficient to break both tabs, the instrument 500 can be rocked back and forth or otherwise manipulated until both tabs are broken off.

FIGS. 6A-6E illustrate an exemplary embodiment of an instrument 600 that can be used, for example, to break off a reduction tab from a bone anchor. As shown, the instrument 600 can include an elongate shaft 602 defined by first and second split shaft portions 602A, 602B, each having a distal opening or slot 604A, 604B configured to receive a reduction tab. While two shafts 602A, 602B are shown, the instrument 600 can include any number of shafts having respective openings for receiving a reduction tab. In use, first and second reduction tabs attached to a bone anchor can be inserted into the openings 604A, 604B, respectively, and the shaft portions 602A, 602B can be independently manipulated to break off the reduction tabs from the bone anchor, e.g., by rotating or angling the shaft portions relative to the bone anchor. A retention element 606A, 606B can be disposed in association with each opening 604A, 604B to help retain the broken off reduction tab within the instrument 600. The shaft portions 602A, 602B can each include a chamber 608A, 608B in which one or more broken off reduction tabs can be captured and stored. For example, the chambers 608A, 608B can be defined between outer surfaces of the shaft portions 602A, 602B and inner surfaces of respective sleeve portions 610A, 610B. The sleeve portions 610A, 610B can together define a sleeve 610 concentrically disposed around the shaft 602. The sleeve portions 610A, 610B can be separate components or can be formed integrally with the shaft portions 602A, 602B. A cap 612 can be attached at a proximal portion of the shaft portions 602A, 602B. The cap 612 can help retain the shafts 602A, 602B to each other prior to a breaking maneuver and/or can be removable to access or to empty the chambers 608A, 608B. The shafts 602A, 602B can together define an inner lumen or cannulation 614 to facilitate use of the instrument 600 over a guidewire or over a guide rod of the type described herein. The cap 612 can include a cannulation that is coaxial with the cannulation 614.

Each shaft 602A, 602B can include a body portion 616A, 616B. The body portions 616A, 616B can together define a central elongate body 616 having a proximal end 616p and a distal end 616d and extending along a central longitudinal axis A5. The body 616 can be generally cylindrical. The body 616 can be solid or, as shown, can be cannulated to allow passage of a guidewire or guide rod therethrough.

The openings 604A, 604B for receiving reduction tabs can be defined by distal portions of the shafts 602A, 602B. For example, the openings 604A, 604B can be defined by respective clearance spaces between outer surfaces of the body portions 616A, 616B and inner surfaces of a shroud 618. The shroud 618 can be defined by respective shroud portions 618A, 618B of the shafts 602A, 602B. The shroud 618 can have a cylindrical or substantially cylindrical exterior surface. The outside diameter of the shroud 618 can be less than or equal to the outside diameter of the outer sleeve 610. The outside diameter of the shroud 618 can be less than or equal to the diameter of a percutaneous or minimally-invasive working channel in which a bone anchor to be used with the instrument 600 is disposed. The inside diameter of the shroud 618 can be equal to or only slightly greater than a maximum outside diameter of the reduction tabs of a bone anchor with which the instrument 600 is to be used. When reduction tabs of a bone anchor are inserted into the openings 604A, 604B, the axis A5 of the shaft 602 can be collinear with a central longitudinal axis of the head or receiver member of the bone anchor.

The first shroud 618A can be integrally or monolithically formed with the first body portion 616A, or can be a separate component attached thereto. The first shroud 618A can be a partial or complete cylindrical tube. The inside diameter of the first shroud 618A can be greater than an outside diameter of the first body portion 616A such that a clearance space is formed therebetween to define the first opening 604A. The difference between the inside diameter of the first shroud 618A and the outside diameter of the first body portion 616A can be selected to define the radial dimension of the first opening 604A. The first opening 604A can have a radial dimension that is equal to or slightly greater than the radial thickness of a reduction tab with which the instrument 600 is to be used. Alternatively, the radial dimension of the first opening 604A can be slightly less than the thickness of the reduction tab, to form an interference fit when the tab is inserted into the opening.

The first shroud 618A can be connected to the first body portion 616A, and can be supported in a spaced relationship from the first body portion, by one or more struts 620A. The struts 620A can extend radially-outward from the first body portion 616A to the first shroud 618A. In the illustrated example, the first body portion 616A includes first and second diametrically-opposed struts 620A that extend from an outer surface of the first body portion to the inner surface of the first shroud 618A. The positioning of the struts 620A and the circumferential width of the struts can be selected to define the circumferential dimension of the first opening 604A. The first opening 604A can have a circumferential dimension that is equal to or slightly greater than the width of a reduction tab with which the instrument 600 is to be used. Alternatively, the circumferential dimension of the first opening 604A can be slightly less than the width of the reduction tab, to form an interference fit when the tab is inserted into the opening.

The illustrated first opening 604A is formed generally as a negative of a section of a tube. While such an opening is shown and described herein, it will be appreciated that the geometry of the first opening 604A can vary depending on the shape and size of the reduction tabs with which the instrument 600 is to be used. The first opening 604A can have a cross section in a plane transverse to the axis A5 that is the same as or substantially the same as a corresponding cross section of the reduction tab.

A first retention element 606A can be disposed in association with the first opening 604A to help retain a broken off reduction tab within the instrument 600. For example, the instrument 600 can include a biased finger 606A configured to interfere with a reduction tab inserted into the first opening 604A to exert a frictional force on the reduction tab. The finger 606A can be formed as cantilevered beam with a contact tip 622A that projects radially-inward from the beam.

The finger or other retention element 606A can be attached to, or can be formed integrally with, any one or more of the first shroud 618A, the first body portion 616A, and the first sleeve portion 610A. The retention element 606A can be attached by welding, adhesives, or other fasteners, such as a through-pin as shown. While a single retention element 606A attached to the first shroud 618A is shown, the first shaft 602A can include a plurality of retention elements. For example, the first shroud 618A can include a first retention element and the first body portion 616A can include a second retention element such that the retention elements are positioned on opposites sides of the first opening 604A. Various other types of retention elements can be used instead or in addition, such as a ball plunger, a leaf spring, a coil spring, ratchet teeth, surface coatings or features, and the like.

The first sleeve portion 610A can be an integral proximal extension of the first shroud 618A as shown, or can be a separate component. In the latter configuration, the distal end of the first shaft 602A can include a radial flange. The flange can define a proximal-facing shoulder against which the first outer sleeve portion 610A can abut to capture and retain the sleeve between the flange and the cap 612. The flange can include a cylindrical boss sized to be received within the distal end of the first sleeve portion 610A to center the first sleeve portion coaxially with the first shaft 602A.

The proximal end of the first shaft 602A can include a mating feature 628A for securing the cap 612 to the instrument 600. For example, as shown, the proximal end of the first shaft 602A can include a channel 628A defined between the first body portion 616A and the first sleeve portion 610A.

The channel 628A can be configured to receive an attachment arm of the cap 612. A recess or throughhole can intersect the channel 628A to receive a detent or other retention feature of the attachment arm. While a snap-fit coupling is shown, it will be appreciated that various other attachment mechanisms can be used instead or in addition, such as a threaded coupling, a bayonet coupling, an interference coupling, etc.

Figure 6A:
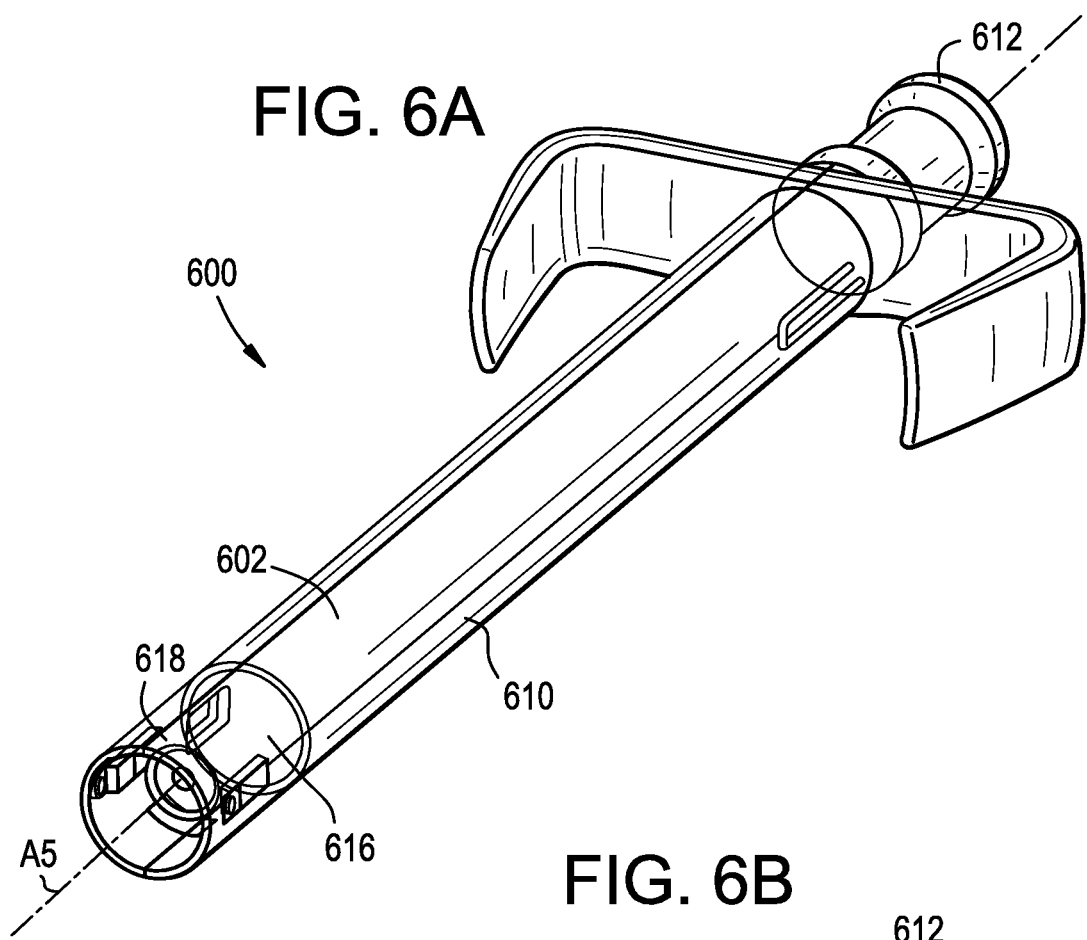
FIG. 6A is a perspective view of an instrument that can be used to break reduction tabs.
Figure 6B:
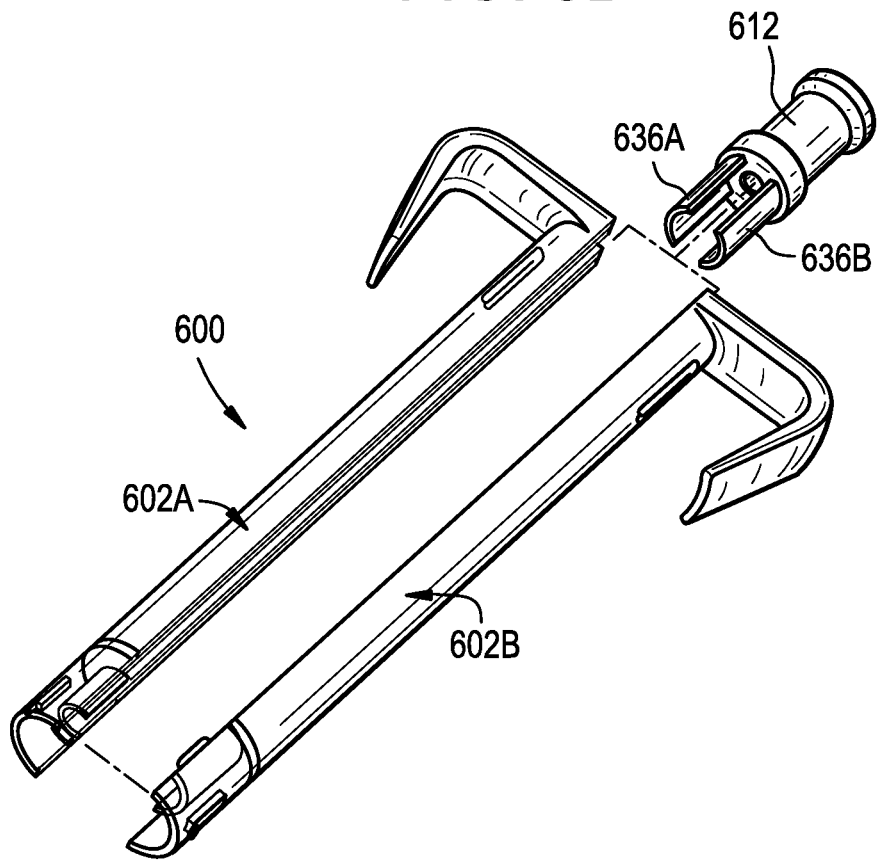
FIG. 6B is an exploded perspective view of the instrument of FIG. 6A.
Figure 6C:
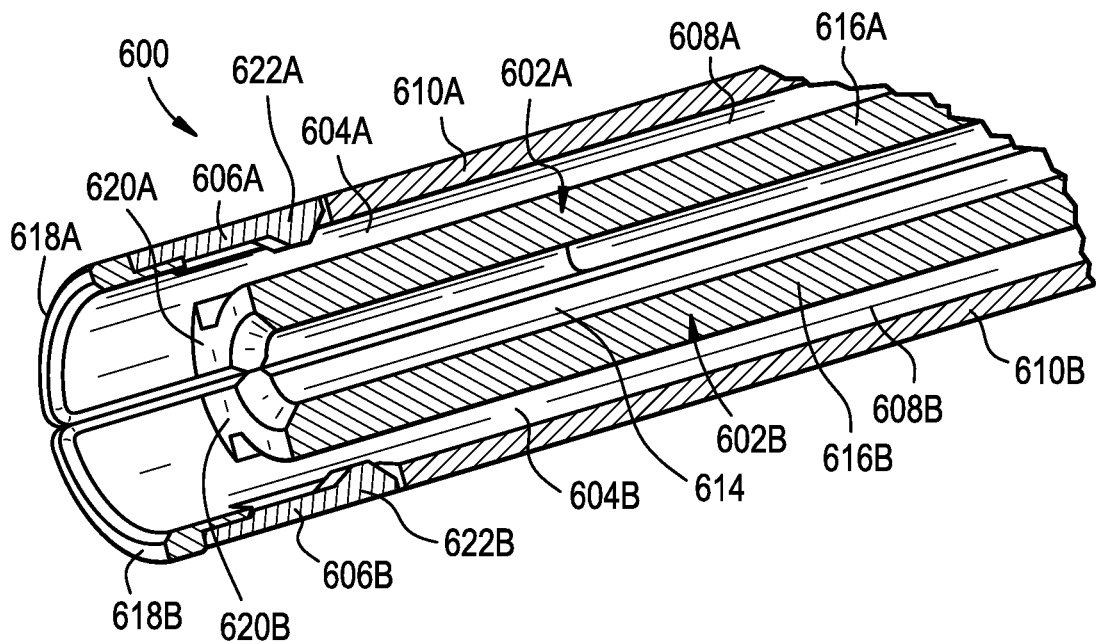
FIG. 6C is a sectional perspective view of the instrument of FIG. 6A.
Figure 6D:
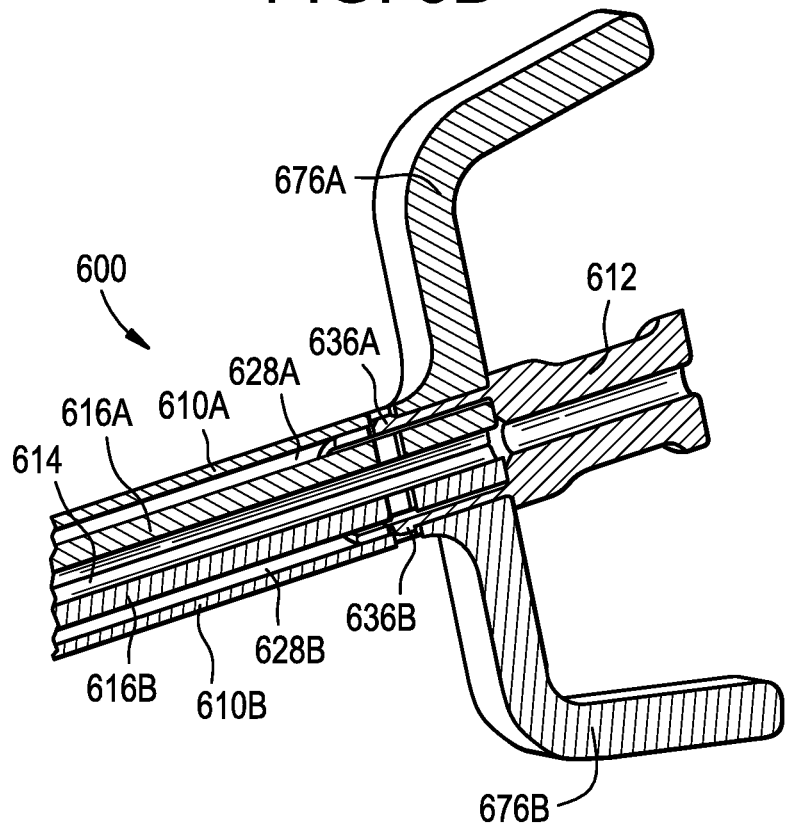
FIG. 6D is another sectional perspective view of the instrument of FIG. 6A.

The proximal end of the first shaft 602A can include a first handle portion 676A to facilitate gripping and manipulation of the first shaft by a user. As shown, the first handle portion 676A can be generally L-shaped with a lateral portion extending generally perpendicular to the first shaft 602A and a longitudinal portion extending generally parallel to the first shaft. The first handle portion 676A can extend distally, e.g., as shown in FIG. 6B, or proximally, e.g., as shown in FIG. 6D. While an L-shaped handle portion 676A is shown, it will be appreciated that the handle portion can have any geometry that allows the handle to be grasped and manipulated by a user.

The second shroud 618B can be integrally or monolithically formed with the second body portion 616B, or can be a separate component attached thereto. The second shroud 618B can be a partial or complete cylindrical tube. The inside diameter of the second shroud 618B can be greater than an outside diameter of the second body portion 616B such that a clearance space is formed therebetween to define the second opening 604B. The difference between the inside diameter of the second shroud 618B and the outside diameter of the second body portion 616B can be selected to define the radial dimension of the second opening 604B. The second opening 604B can have a radial dimension that is equal to or slightly greater than the radial thickness of a reduction tab with which the instrument 600 is to be used. Alternatively, the radial dimension of the second opening 604B can be slightly less than the thickness of the reduction tab, to form an interference fit when the tab is inserted into the opening.

The second shroud 618B can be connected to the second body portion 616B, and can be supported in a spaced relationship from the second body portion, by one or more struts 620B. The struts 620B can extend radially-outward from the second body portion 616B to the second shroud 618B. In the illustrated example, the second body portion 616B includes first and second diametrically-opposed struts 620B that extend from an outer surface of the second body portion to the inner surface of the second shroud 618B. The positioning of the struts 620B and the circumferential width of the struts can be selected to define the circumferential dimension of the second opening 604B. The second opening 604B can have a circumferential dimension that is equal to or slightly greater than the width of a reduction tab with which the instrument 600 is to be used. Alternatively, the circumferential dimension of the second opening 604B can be slightly less than the width of the reduction tab, to form an interference fit when the tab is inserted into the opening.

The illustrated second opening 604B is formed generally as a negative of a section of a tube. While such an opening is shown and described herein, it will be appreciated that the geometry of the second opening 604B can vary depending on the shape and size of the reduction tabs with which the instrument 600 is to be used. The second opening 604B can have a cross section in a plane transverse to the axis A5 that is the same as or substantially the same as a corresponding cross section of the reduction tab.

A second retention element 606B can be disposed in association with the second opening 604B to help retain a broken off reduction tab within the instrument 600. For example, the instrument 600 can include a biased finger 606B configured to interfere with a reduction tab inserted into the second opening 604B to exert a frictional force on the reduction tab. The finger 606B can be formed as cantilevered beam with a contact tip 622B that projects radially-inward from the beam.

The finger or other retention element 606B can be attached to, or can be formed integrally with, any one or more of the second shroud 618B, the second body portion 616B, and the second sleeve portion 610B. The retention element 606B can be attached by welding, adhesives, or other fasteners, such as a through-pin as shown. While a single retention element 606B attached to the second shroud 618B is shown, the second shaft 602B can include a plurality of retention elements. For example, the second shroud 618B can include a first retention element and the second body portion 616B can include a second retention element such that the retention elements are positioned on opposites sides of the second opening 604B. Various other types of retention elements can be used instead or in addition, such as a ball plunger, a leaf spring, a coil spring, ratchet teeth, surface coatings or features, and the like.

The second sleeve portion 610B can be an integral proximal extension of the second shroud 618B as shown, or can be a separate component. In the latter configuration, the distal end of the second shaft 602B can include a radial flange. The flange can define a proximal-facing shoulder against which the second outer sleeve portion 610B can abut to capture and retain the sleeve between the flange and the cap 612. The flange can include a cylindrical boss sized to be received within the distal end of the second sleeve portion 610B to center the second sleeve portion coaxially with the second shaft 602B.

The proximal end of the second shaft 602B can include a mating feature 628B for securing the cap 612 to the instrument 600. For example, as shown, the proximal end of the second shaft 602B can include a channel 628B defined between the second body portion 602B and the second sleeve portion 610B. The channel 628B can be configured to receive an attachment arm of the cap 612. A recess or throughhole can intersect the channel 628B to receive a detent or other retention feature of the attachment arm. While a snap-fit coupling is shown, it will be appreciated that various other attachment mechanisms can be used instead or in addition, such as a threaded coupling, a bayonet coupling, an interference coupling, etc.

The proximal end of the second shaft 602B can include a second handle portion 676B to facilitate gripping and manipulation of the second shaft by a user. As shown, the second handle portion 676B can be generally L-shaped with a lateral portion extending generally perpendicular to the second shaft 602B and a longitudinal portion extending generally parallel to the second shaft. The second handle portion 676B can extend distally, e.g., as shown in FIG. 6B, or proximally, e.g., as shown in FIG. 6D. While an L-shaped handle portion 676B is shown, it will be appreciated that the handle portion can have any geometry that allows the handle to be grasped and manipulated by a user.

The sleeve 610 can be formed by first and second sleeve portions 610A, 610B that together define an elongate cylindrical tube. The inside diameter of the sleeve portions 610A, 610B can be greater than an outside diameter of the body portions 616A, 616B of the shafts 602A, 602B, such that a clearance space is formed therebetween to define the chamber 608. The length and volume of the chamber 608 can be selected to fit one or more broken-off reduction tabs therein.

In some embodiments, the chamber 608 can be sized to hold a plurality of reduction tabs simultaneously. The sidewall of the sleeve 610 can be solid or can include one or more openings therein. The openings can allow visibility into the chamber 608, e.g., to allow a user to assess the number of reduction tabs in the chamber or the inserted depth of a reduction tab into the chamber. The openings can also facilitate cleaning and sterilization of the instrument 600 by allowing a fluid to easily flow into and out of the chamber 608 during such processes. The chamber 608 can be a single continuous chamber defined by the first and second shafts 602A, 602B. Alternatively, each shaft 602A, 602B can include an independent chamber 608A, 608B.

The cap 612 can include a mating feature 636 for securing the cap to the instrument 600. For example, as described above, the cap 612 can include first and second attachment arms 636A, 636B configured to be received within and secured to the channels 628A, 628B of the shafts 602A, 602B. The attachment arms 636A, 636B can be formed as male projections, each shaped as a section of a tube. An outer surface of the cap 612 can include gripping features to facilitate force application to the cap by the user, e.g., to pull the cap proximally to disengage the mating features of the cap and to separate the cap from the shafts 602A, 602B.

Figure 6E:
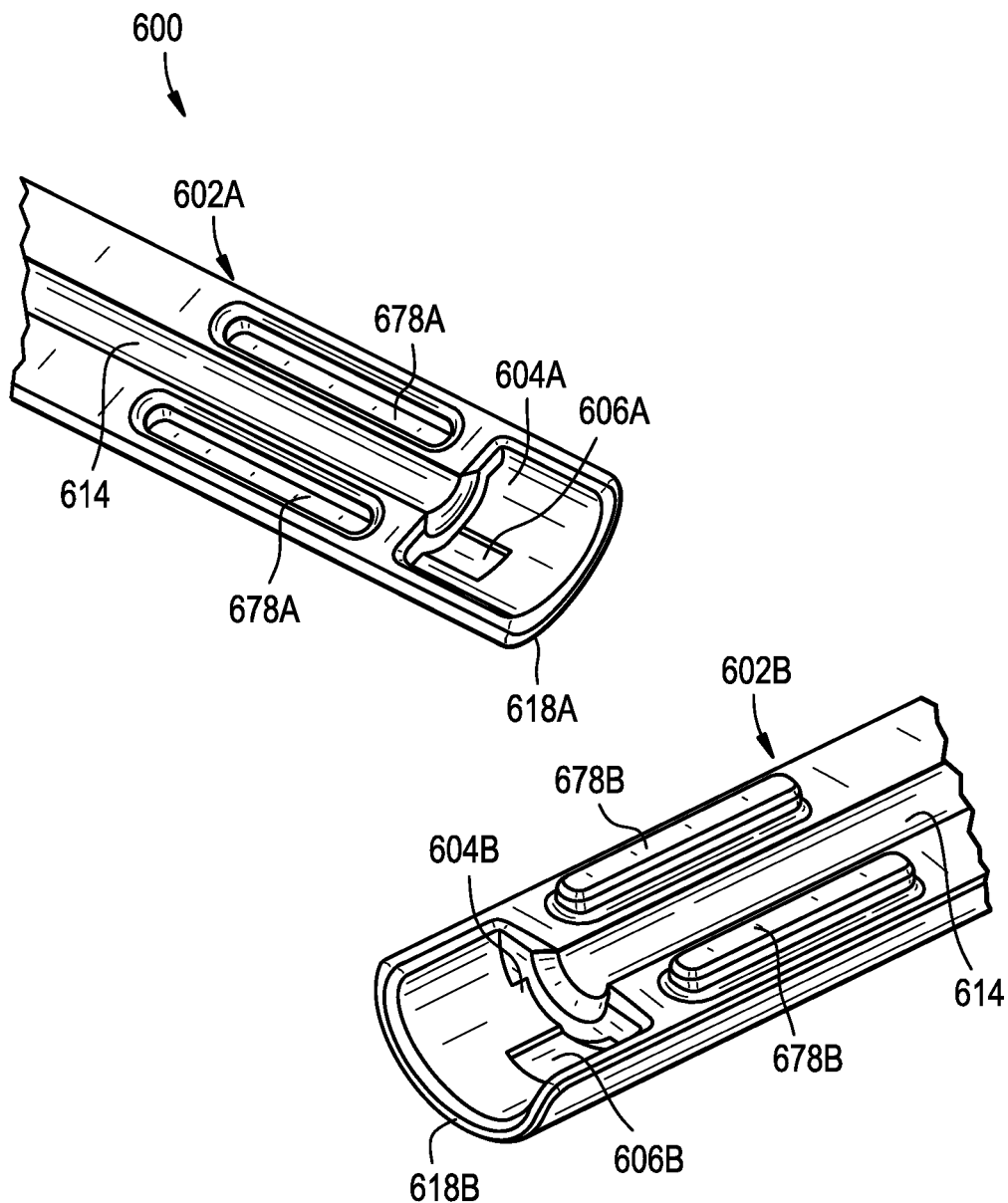
FIG. 6E is another exploded perspective view of the instrument of FIG. 6A.

The instrument 600 can include alignment features for maintaining the shafts 602A, 602B in a desired position with respect to one another prior to breaking a reduction tab, e.g., a position in which the shafts are parallel to one another and directly abut one another. For example, the instrument 600 can include a proximal alignment feature defined by the interaction between the cap 612 and the shafts 602A, 602B when the cap is assembled to the shafts. When the cap 612 is mated to the shafts 602A, 602B, interaction between the arms 636A, 636B and the channels 628A, 628B can limit or prevent relative movement between the proximal ends of the shafts. As another example, the instrument 600 can include a distal alignment feature configured to limit or prevent relative movement between the distal ends of the shafts 602A, 602B. As shown in FIG. 6E, the shafts 602A, 602B can include complementary male and female features for limiting certain movement between the shafts when mated. The illustrated arrangement includes first and second grooves 678A formed in an inner surface of the first shaft 602A and first and second rails 678B formed in an inner surface of the second shaft 602B. When the rails 678B are received within the grooves 678A, relative longitudinal translation between the first and second shafts 602A, 602B can be limited or prevented. While two sets of male/female features are shown, the instrument can include any number of such features, or can include other types of alignment features.

Exemplary instruments for breaking reduction tabs are disclosed in U.S. Pat. No. 9,402,673 of Cormier et al., entitled DEVICES AND METHODS FOR BREAKING AND RETAINING SURGICAL REDUCTION TABS, which is hereby incorporated by reference herein. The instrument 600 can include any of the features or variations described in the above reference.

Figure 7A:
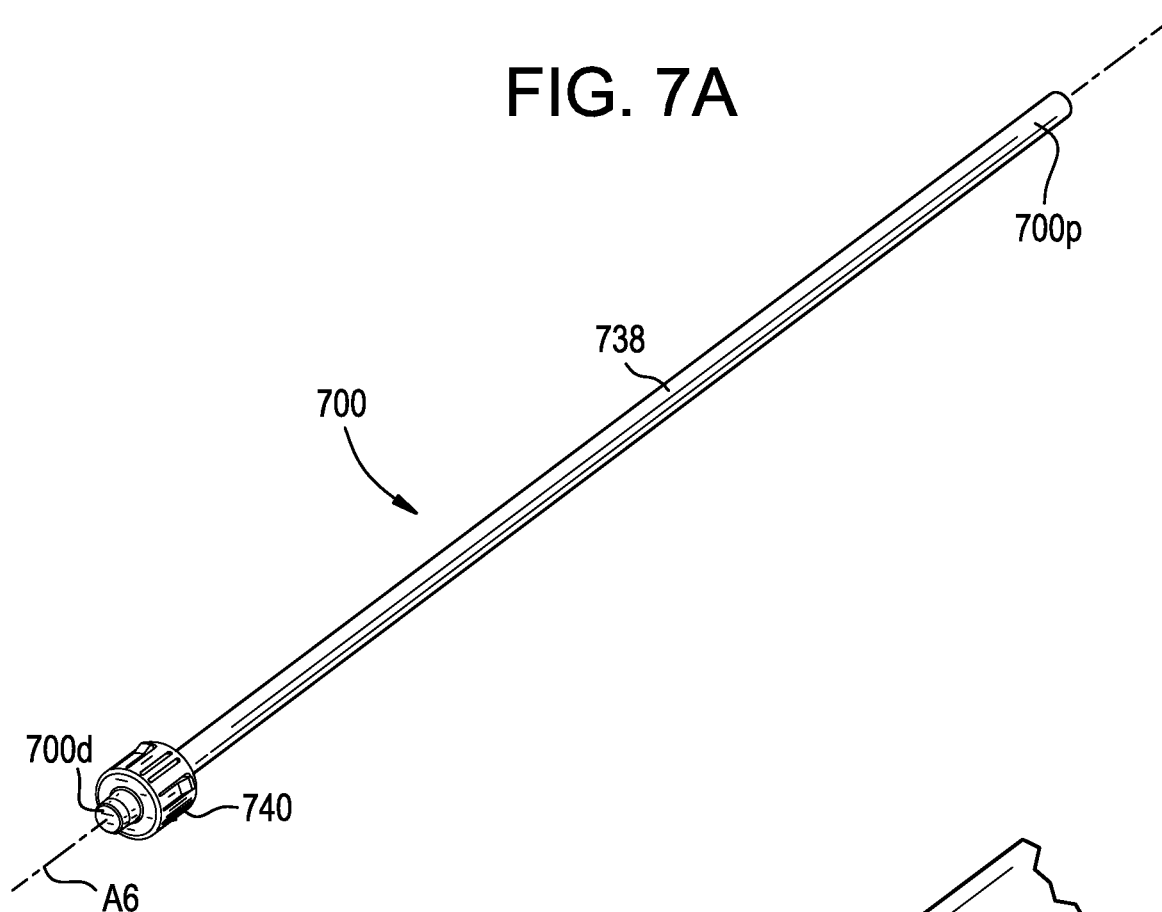
FIG. 7A is a perspective view of a guide rod.
Figure 7B:
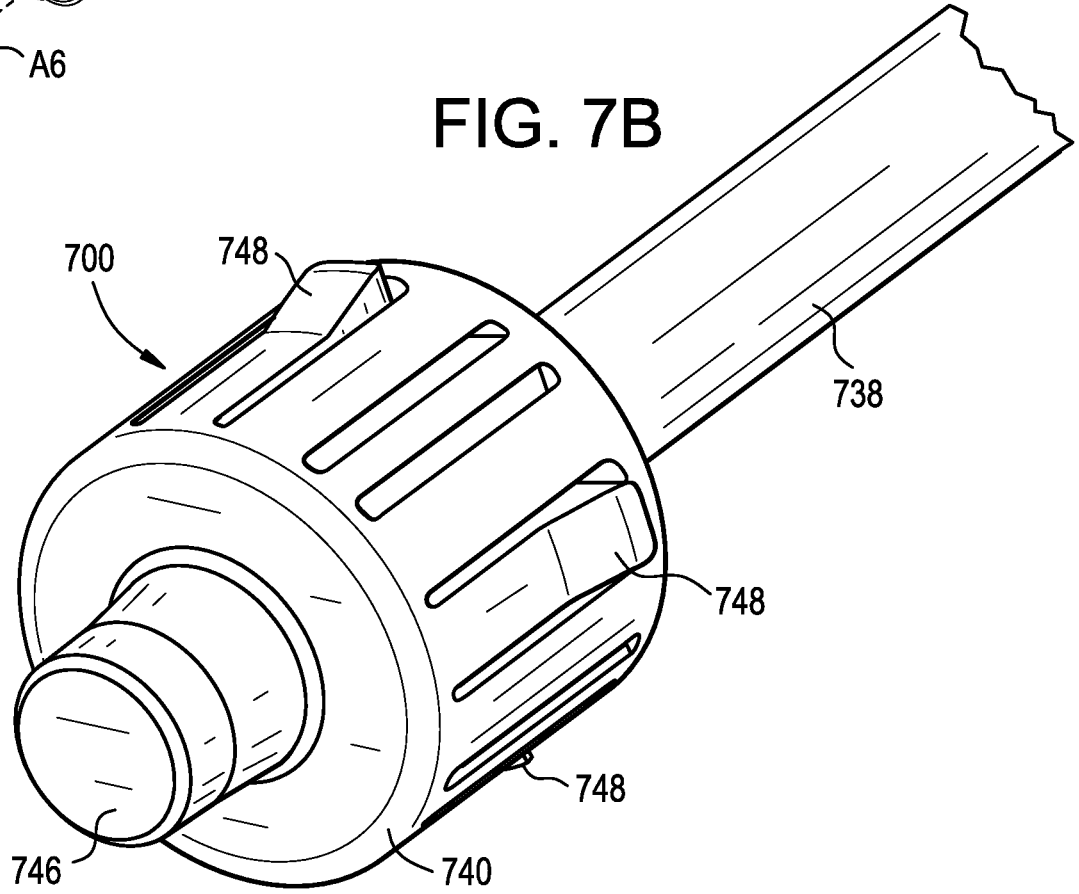
FIG. 7B is another perspective view of the guide rod of FIG. 7A.

FIGS. 7A-7B illustrate an exemplary guide rod 700 that can be used with any of the tab breaker instruments described herein, e.g., the instrument 600 described above. The guide rod 700 can include a distal portion configured to be secured or docked to an implanted bone anchor and a proximal guide portion over which an instrument can be advanced into proximity to the bone anchor. The guide rod 700 can be particularly useful in percutaneous or minimally-invasive procedures in which it may be difficult to visualize the implanted bone anchor and to align a reduction tab of the bone anchor with the opening of a tab breaker instrument.

The guide rod 700 can include proximal and distal ends 700p, 700d that define a central longitudinal axis A6 therebetween. The guide rod 700 can include an elongate guide shaft 738 and a distal plug 740. The guide shaft 738 can be cylindrical and can be sized to be received within a cannulation of an instrument, e.g., the cannulation 614 of the instrument 600 described above.

The distal plug 740 can be fixedly coupled to the guide shaft 738. The plug 740 can include features for aligning the plug with a bone anchor. For example, the plug 740 can include a distal projection 746 sized to fit within the drive recess of the shank of the bone anchor and/or within the drive recess of a set screw or other fastener coupled to the bone anchor.

The plug 740 can include features for securing the guide rod 700 to a bone anchor. For example, the plug 740 can include one or more radial projections 748 configured to engage with corresponding features of the bone anchor, e.g., internal threads of the reduction tabs or of the receiver head of the bone anchor. The projections 748 can click, snap, or thread into engagement with the threads of the bone anchor to resist or prevent withdrawal of the plug 740 from the bone anchor. The illustrated projections 748 are formed as cantilevered spring arms, though it will be appreciated that various other arrangements can be used instead or in addition. While four projections 748 spaced equally about the circumference of the plug 740 are shown, the plug can include any number of projections at any desired spacing. Increasing the number of projections 748 can advantageously increase the number of rotational positions about the axis A6 at which one or more projections are aligned with the threads of the bone anchor to secure the guide rod 700 to the bone anchor.

Figure 8A:
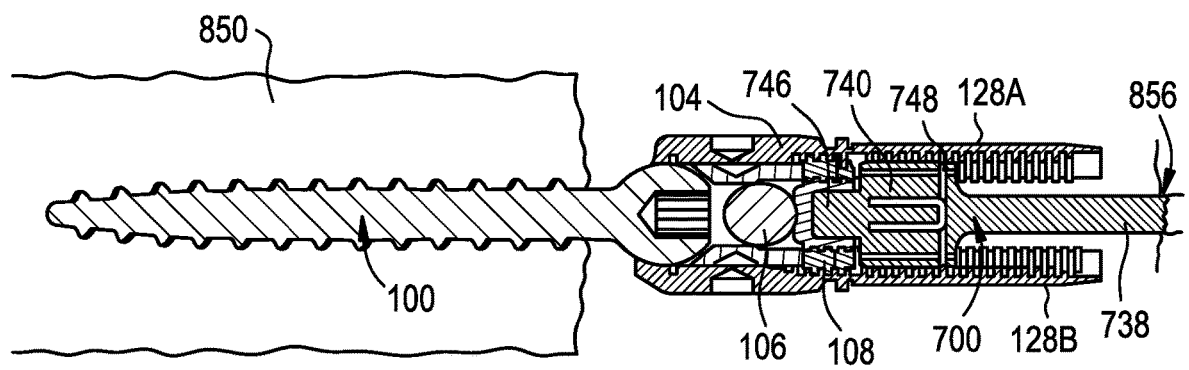
FIG. 8A is a sectional side view of a bone anchor with the guide rod of FIG. 7A attached thereto.
Figure 8B:
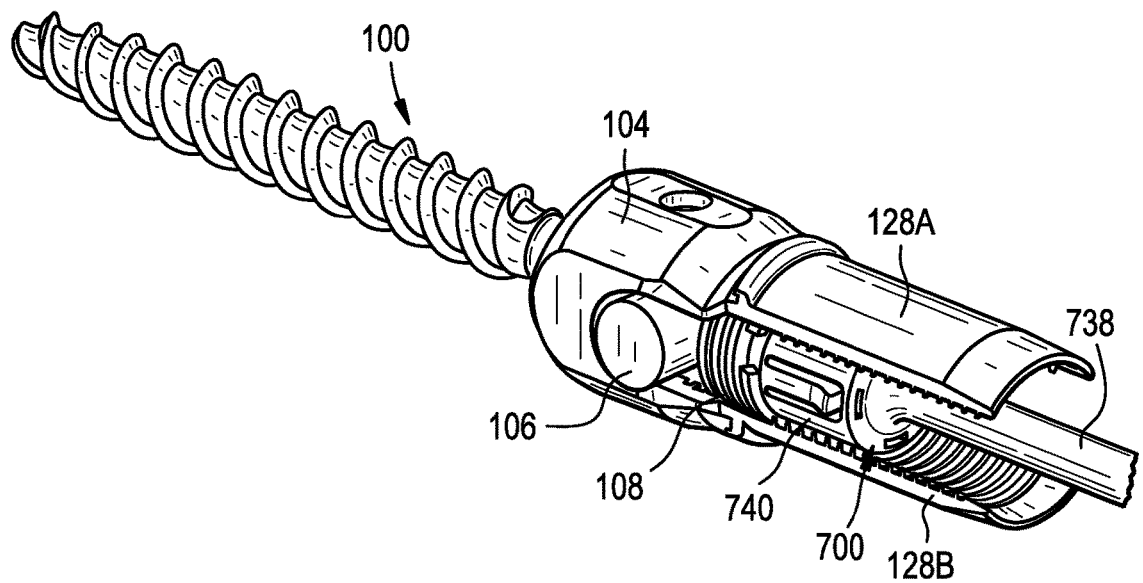
FIG. 8B is a perspective view of the bone anchor and guide rod of FIG. 8A.

An exemplary method of using the instrument 600 is shown in FIGS. 8A-8H. As shown in FIGS. 8A-8B, a bone anchor 100 having one or more reduction tabs 128 can be driven into a bone 850 of a patient, e.g., a pedicle or lateral mass of a patient's vertebra. Using known techniques, a rod or other fixation element 106 can be seated in the bone anchor 100, and a fastener 108 can be applied to the bone anchor to retain the rod therein. The reduction tabs 128 can be used to facilitate the above steps. For example, a threaded reduction instrument (not shown) can be advanced along internal threads of the reduction tabs 128 to bear against the rod 106 and urge the rod distally into the recess of the bone anchor 100. As another example, the fastener 108 can be engaged with the threads of the reduction tabs 128 and rotated to advance the fastener and the rod 106 distally, urging the rod towards the recess of the bone anchor 100 and eventually moving the fastener into the threads of the bone anchor receiver 104.

As described above, an access device can be coupled to the bone anchor 100 to establish a working channel between the bone anchor and a skin incision 856. The access device can be attached to the bone anchor 100 before or after driving the bone anchor into the bone 850, and before or after seating the rod 106 and fastener 108 in the bone anchor. Exemplary access devices are disclosed in U.S. Pat. No. 7,179,261 of Sicvol et al., entitled PERCUTANEOUS ACCESS DEVICES AND BONE ANCHOR ASSEMBLIES, which is hereby incorporated by reference herein.

A guidewire or a guide rod can be used to help align the instrument 600 with the reduction tabs 128 of the bone anchor 100. For example, a guide rod 700 of the type described herein can be inserted through the access device and advanced towards the bone anchor 100. The plug 740 of the guide rod 700 can be advanced distally relative to the bone anchor 100 until the alignment projection 746 of the plug is seated in the drive recess of the fastener 108 of the bone anchor. As the plug 740 is advanced distally, the radial projections 748 of the plug can engage with the interior threads of the reduction tabs 128 to retain the plug to the bone anchor 100. For example, interference can exist between the projections 748 and the threads of the reduction tabs 128, such that the projections and the beams to which they are mounted deflect radially inward as the plug 740 is advanced across each crest of the thread. Once the projection 748 passes the crest, the beam and the projection 748 can spring radially outward to seat the projection in the root of the thread. The distal-facing surface of the projections 748 can be ramped, curved, or otherwise tapered to facilitate deflection of the projections during distal advancement. The proximal-facing surface of the projections 748 can be planar and can extend perpendicular to the axis A6 to resist or prevent proximal retraction of the plug 740. The thread and the projections 748 can thus interlock to secure the plug 740 to the reduction tabs 128 or to the arms of the bone anchor 100.

Once the guide rod 700 is in place, or at any other time desired by the user, the access device can be separated from the bone anchor 100 and removed from the incision 856. As shown in FIGS. 8A-8B, the guide rod 700 can be left in place when the access device is removed, serving as a guide for advancing the instrument 600 into engagement with the reduction tabs 128 of the bone anchor 100.

Figure 8C:
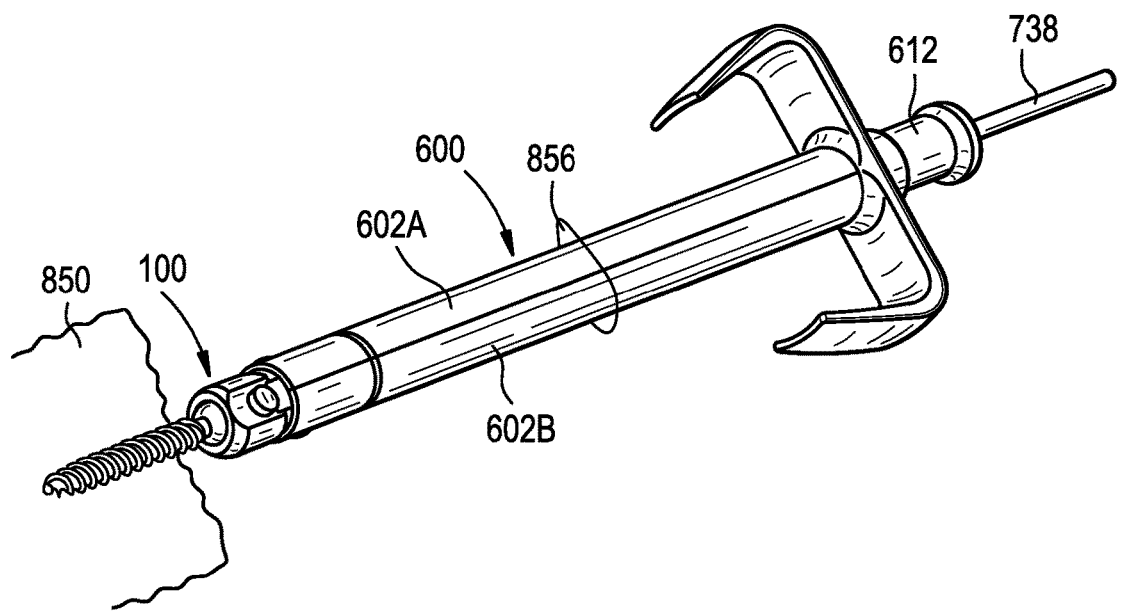
FIG. 8C is a perspective view of the bone anchor and guide rod of FIG. 8A with an extension tab of the bone anchor received in the instrument of FIG. 6A.
Figure 8D:
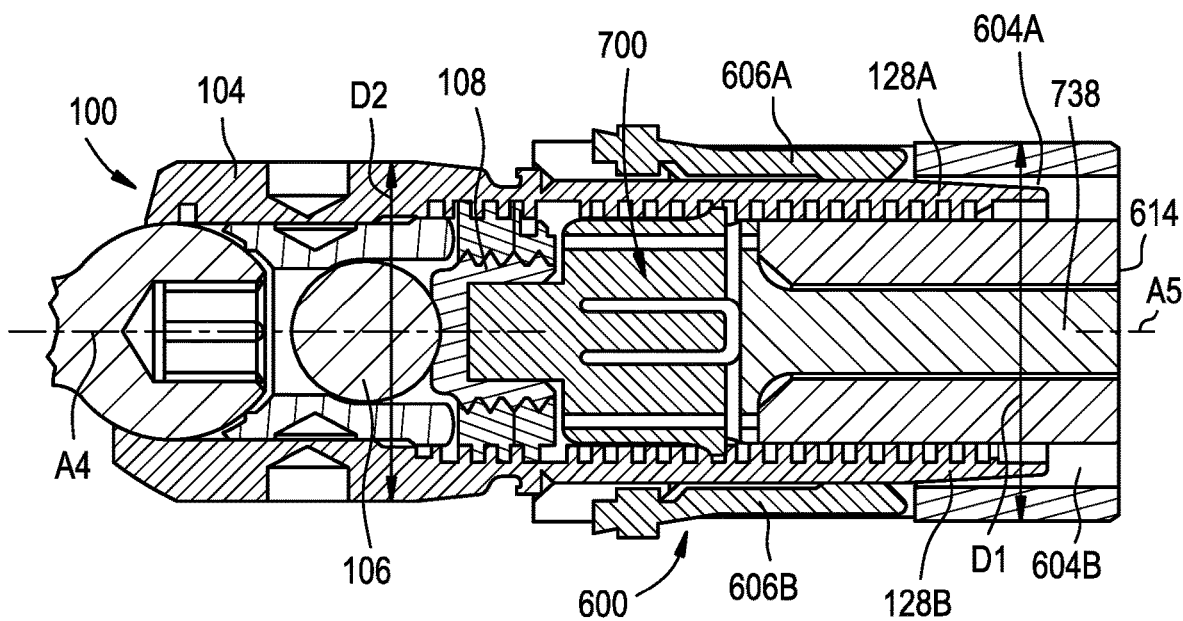
FIG. 8D is a sectional side view of the bone anchor, guide rod, and instrument of FIG. 8C.
Figure 8E:
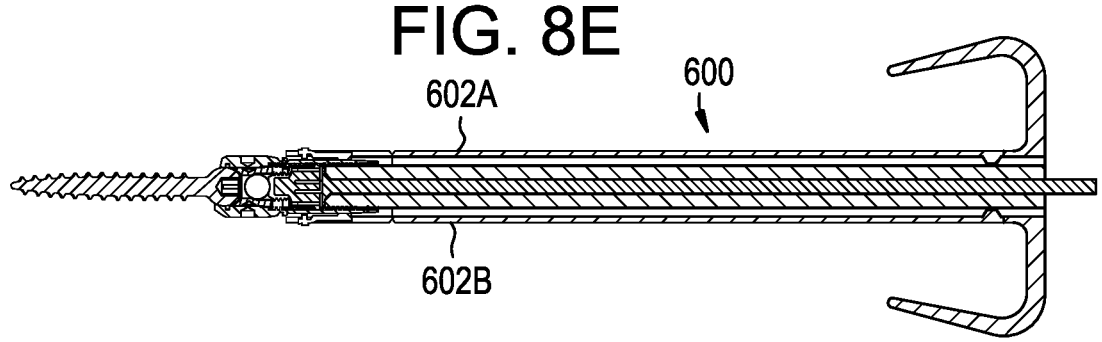
FIG. 8E is another sectional side view of the bone anchor, guide rod, and instrument of FIG. 8C.
Figure 8F:
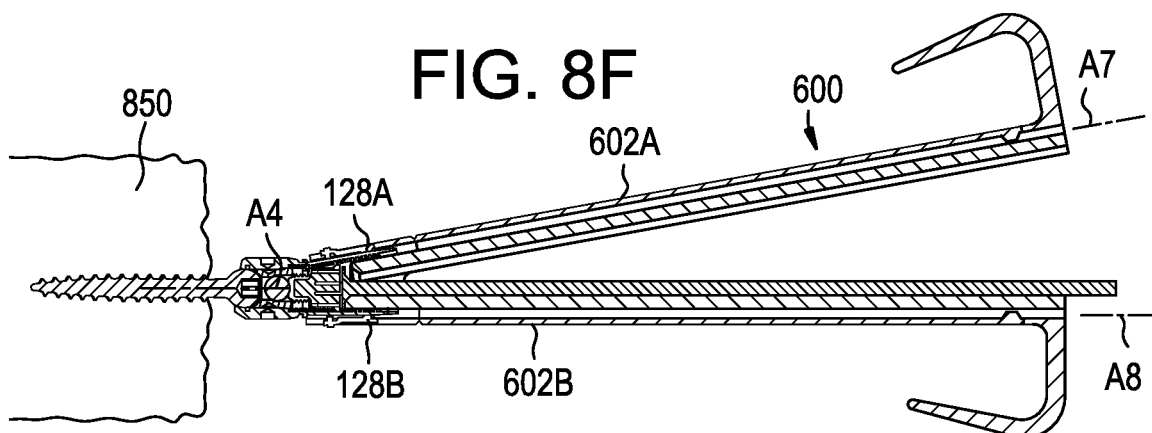
FIG. 8F is a sectional side view of the bone anchor, guide rod, and instrument of FIG. 8C, with the instrument manipulated to break the reduction tab.
Figure 8G:
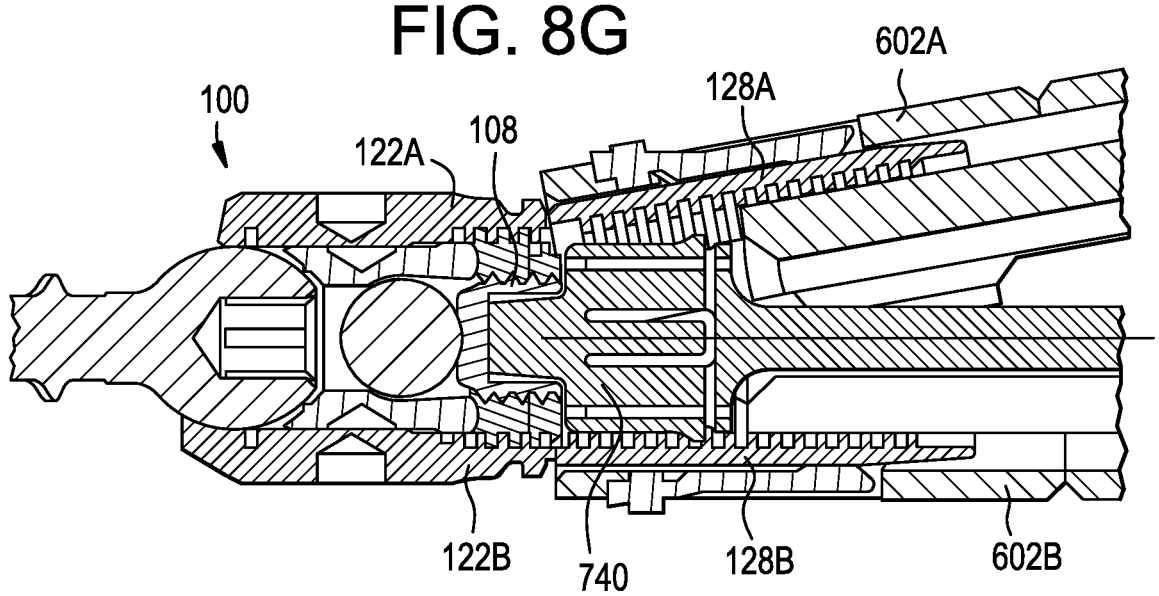
FIG. 8G is another sectional side view of the bone anchor, guide rod, and instrument of FIG. 8C, with the instrument manipulated to break the reduction tab.
Figure 8H:
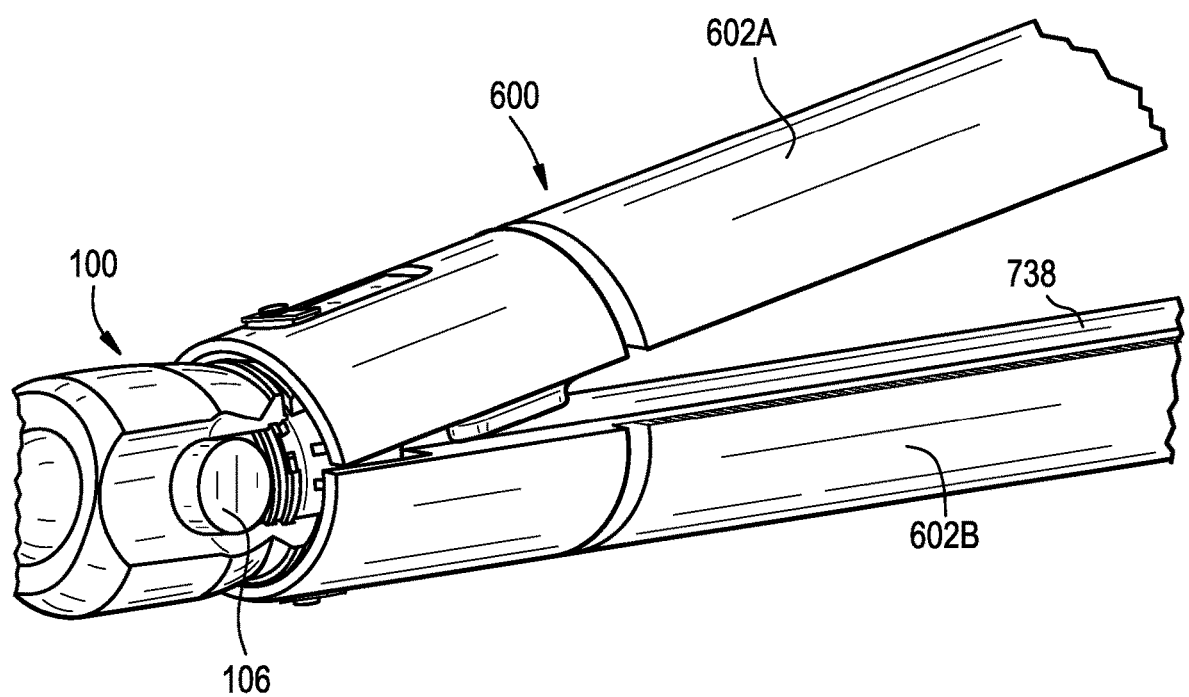
FIG. 8H is a perspective view of the bone anchor, guide rod, and instrument of FIG. 8C, with the instrument manipulated to break the reduction tab.

When the user desires to break off a reduction tab 128 of the bone anchor 100, the instrument 600 can be passed over the guide rod 700 and positioned with respect to the bone anchor as shown in FIGS. 8C-8D. In particular, the guide shaft 738 of the guide rod 700 can be inserted through the cannulation 614 of the instrument 600. The instrument 600 can then be translated distally along the guide rod 700 to move the distal end of the instrument into the incision 856 and into proximity to the bone anchor 100. The instrument 600 can be further advanced to slide the first and second reduction tabs 128A, 128B into the openings 604A, 604B of the instrument. Insertion of the reduction tabs 128A, 128B into the openings 604A, 604B can cause deflection of the retaining elements 606A, 606B, thereby exerting a frictional force on the reduction tabs to help hold the reduction tabs within the instrument 600 after they are broken off. The use of a guide rod 700 can thus help automatically align the reduction tabs 128A, 128B with the openings 604A, 604B. This can be particularly advantageous when the instrument 600 is used with reduction tabs 128 which are shorter than the depth of the incision 856 in which they are placed (such as the illustrated reduction tabs).

With the instrument 600 positioned as shown, the instrument is ready to be used to break off the reduction tabs 128. In this ready position, as shown, the central longitudinal axis A5 of the instrument 600 can be collinear with a central longitudinal axis A4 of the receiver head 104 of the bone anchor 100. This coaxial arrangement of the instrument 600 with the receiver member 104 can advantageously reduce the degree to which tissue around the bone anchor 100 must be cut or retracted to accommodate the instrument 600 during use. This is in contrast with some conventional tab breaker instruments, in which the central longitudinal axis of the tab breaker is laterally offset from the central longitudinal axis of the receiver while in the above-described ready position, requiring additional tissue resection or retraction to the side of the bone anchor to accommodate the instrument.

While a coaxial arrangement can be advantageous in some embodiments, in other embodiments the central longitudinal axis A5 of the instrument 600 can be laterally offset from the central longitudinal axis A4 of the receiver 104.

Also in this ready position, the maximum outer transverse dimension D1 of the instrument 600 can be less than the maximum outer transverse dimension D2 of the bone anchor 100, equal to the maximum outer dimension of the bone anchor, or only slightly greater than the maximum outer dimension of the bone anchor. The maximum outer dimension D1 of the instrument 600 can be less than about 15% greater than the maximum outer dimension D2 of the bone anchor 100, less than about 10% greater than the maximum outer dimension of the bone anchor, and/or less than about 5% greater than the maximum outer dimension of the bone anchor. By limiting the dimension D1, the size of the incision 856 can advantageously be kept small, e.g., only as large as needed to insert the bone anchor 100 using a typical percutaneous approach. This is in contrast with some conventional tab breaker instruments, which can have a maximum outer dimension that is significantly greater than a maximum outer dimension of the bone anchor 100. While a reduced dimension D1 can be advantageous in some embodiments, in other embodiments the dimension D1 can be significantly greater than the maximum outer dimension D1 of the bone anchor.

FIGS. 8E-8H illustrate an exemplary manipulation of the instrument 600 to break the reduction tabs 128A, 128B received within the openings 604A, 604B. As shown, the cap 612 can be removed from the instrument 600 to allow the shafts 602A, 602B to be separated and angled relative to one another. The first shaft 602A can be angled relative to the bone anchor 100 such that a central longitudinal axis A7 of the first shaft 602A is obliquely angled with respect to the central longitudinal axis A4 of the bone anchor 100. With the reduction tab 128A captured within the opening 604A of the first shaft 602A, this movement can cause the reduction tab to bend relative to the arm 122A from which it extends until the reduction tab breaks off from the arm. Even with the now-broken reduction tab 128A being separated from the plug 740, the engagement between the plug and the fastener 108 and the engagement between the plug and the remaining reduction tab 128B can be sufficient to keep the plug in place within the bone anchor 100. Once separated from the bone anchor 100, the reduction tab 128A can be held within the opening 604A by the retaining element 606A of the instrument 600. While an outward angling movement is shown, in other examples the first shaft 602A can be angled in other directions to break the tab 128A or rotated about the axis A7 to break the tab.

To break off the remaining reduction tab 128B, the second shaft 602B can be angled relative to the bone anchor 100 such that a central longitudinal axis A8 of the second shaft 602B is obliquely angled with respect to the central longitudinal axis A4 of the bone anchor 100. With the reduction tab 128B captured within the opening 604B of the second shaft 602B, this movement can cause the reduction tab to bend relative to the arm 122B from which it extends until the reduction tab breaks off from the arm. Even with the now-broken reduction tab 128B being separated from the plug 740, the engagement between the plug and the fastener 108 can be sufficient to keep the plug in place within the bone anchor 100. Once separated from the bone anchor 100, the reduction tab 128B can be held within the opening 604B by the retaining element 606B of the instrument 600. While an outward angling movement is shown, in other examples the second shaft 602B can be angled in other directions to break the tab 128B or rotated about the axis A8 to break the tab.

The above steps can be repeated to break off the reduction tabs of one or more additional bone anchors. Insertion of subsequent reduction tabs into the openings 604A, 604B can force previously-broken reduction tabs disposed therein proximally into the chamber 608 where they can be retained and stored. When the chamber 608 is full, or at any other desired time, the cap 612 of the instrument 600 can be removed and the chamber contents can be emptied through the proximal end of the instrument.

Once both reduction tabs 128 are broken off from the bone anchor 100, or at any other desired time, the instrument 600 and the guide rod 700 can be withdrawn proximally from the bone anchor 100 and removed from the surgical site. The surgical procedure can then be completed and the incision closed using known techniques.

In a variation on the above method, the tabs 128A, 128B can be broken by sliding the shafts 602A, 602B longitudinally relative to one another instead of or in addition to splitting the shafts apart from one another. In such an arrangement, the length of the female features 678A can be greater than the length of the male features 678B to allow relative longitudinal translation between the shafts 602A, 602B. In operation, the first and second shafts 602A, 602B can be tilted in the same direction relative to the bone anchor receiver 104 while remaining in direct abutment with one another, with the shafts sliding longitudinally relative to each other. Both tabs 128A, 128B can be broken in a single one of such tilting motions, or the movement can be repeated as many times as needed to break the tabs, e.g., by rocking the instrument 600 back and forth in different directions. If the guide rod 700 interferes with this type of movement, the guide rod can be removed prior to breaking the tabs, or can be withdrawn proximally to provide clearance space for rocking the shafts 602A, 602B.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The instruments disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the instruments disclosed herein can be rigid or flexible. One or more components or portions of the instrument can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of breaking a reduction tab from a bone anchor implanted in a bone such as the pedicle or lateral mass of a human spine, it will be appreciated that the methods and devices disclosed herein can be used with any human or animal bone, implant, non-living object, and so forth.

Although specific embodiments are described above, it should be understood that numerous changes may be made within the spirit and scope of the concepts described.

The invention claimed is:

1. An instrument for breaking reduction tabs, the instrument comprising:
   a first shaft having a first opening configured to receive a reduction tab;
   a second shaft having a second opening configured to receive a reduction tab; and
   a cap that retains proximal ends of the shafts to one another;
   wherein the cap is removable to allow the first and second shafts to be independently spread apart from one other to break reduction tabs received within the openings of the first and second shafts;
   wherein the first opening is defined between an outer surface of a body portion of the first shaft and an inner surface of a first shroud extending distally from the body portion; and
   wherein the second opening is defined between an outer surface of a body portion of the second shaft and an inner surface of a second shroud extending distally from the body portion.

2. The instrument of claim 1, further comprising a first retention element disposed in association with the first opening to retain a broken reduction tab within the first opening and a second retention element disposed in association with the second opening to retain a broken reduction tab within the second opening.

3. The instrument of claim 1, wherein the first and second shafts together define an inner cannulation that is coaxial with a cannulation of the cap.

4. The instrument of claim 1, wherein the first and second openings are formed as a negatives of respective sections of a tube.

5. The instrument of claim 1, wherein the first and second shrouds are connected to their respective body portions by opposed struts.

6. The instrument of claim 1, wherein the first and second shrouds define a complete tube.

7. The instrument of claim 1, wherein the instrument includes a first chamber in communication with the first opening and configured to store broken reduction tabs and a second chamber in communication with the second opening and configured to store broken reduction tabs.

8. The instrument of claim 7, wherein the first and second chambers are defined between inner body portions of the first and second shafts and outer sleeve portions of the first and second shafts.

9. The instrument of claim 1, wherein the first shaft includes an inner abutment surface that contacts a counterpart inner abutment surface of the second shaft, and wherein the first and second shafts include outer surfaces that collectively define a complete tube.

10. The instrument of claim 9, wherein the inner surfaces are substantially planar.

11. The instrument of claim 9, wherein the inner surface of the first shaft includes a male mating feature received within a female mating feature of the inner surface of the second shaft.

12. The instrument of claim 1, wherein the cap includes first and second arms received within corresponding channels formed in proximal ends of the first and second shafts.

13. A reduction tab breaking system, comprising:
- a bone anchor having a receiver head with a central longitudinal axis and first and second reduction tabs extending proximally from the receiver head; and
- an instrument for breaking the reduction tabs off of the receiver head, the instrument comprising a shaft that defines an opening sized to receive one of the reduction tabs therein;
- wherein a central longitudinal axis of the shaft is collinear with the central longitudinal axis of the receiver head when one of the reduction tabs is received within the opening.

14. The system of claim 13, wherein the instrument has a maximum outer transverse dimension that is less than or equal to a maximum outer transverse dimension of the bone anchor.

15. The system of claim 13, further comprising a guide rod having a distal portion configured to be secured to the bone anchor and a proximal guide shaft received within a central cannulation of the instrument to guide one of the reduction tabs of the bone anchor into the opening.

16. The system of claim 15, wherein the distal portion of the guide rod comprises a plug with a distal projection sized to be received within a drive recess of a fastener of the bone anchor and one or more radial projections configured to engage threads of the bone anchor.

17. The system of claim 16, wherein the plug is rotatable relative to the guide shaft about an axis perpendicular to a longitudinal axis of the guide shaft.

18. The system of claim 13, wherein the instrument includes a shroud that defines at least a portion of the opening, the shroud having an inside diameter that is substantially equal to an outside diameter of the first and second reduction tabs.

19. The system of claim 13, wherein the opening has a cross-section in a plane transverse to a central longitudinal axis of the instrument that is substantially the same as a corresponding cross section of one of the first and second reduction tabs.

20. An instrument for breaking reduction tabs, the instrument comprising:
- a first shaft having a first opening configured to receive a reduction tab;
- a second shaft having a second opening configured to receive a reduction tab; and
- a cap that retains proximal ends of the shafts to one another;
- wherein the cap is removable to allow the first and second shafts to be independently spread apart from one other to break reduction tabs received within the openings of the first and second shafts;
- wherein the instrument includes a first chamber in communication with the first opening and configured to store broken reduction tabs and a second chamber in communication with the second opening and configured to store broken reduction tabs; and
- wherein the first and second chambers are defined between inner body portions of the first and second shafts and outer sleeve portions of the first and second shafts.

* * * * *